US010925901B2

(12) United States Patent
Dietz et al.

(10) Patent No.: US 10,925,901 B2
(45) Date of Patent: Feb. 23, 2021

(54) COMPOSITIONS CONTAINING PLATELET CONTENTS

(71) Applicant: Mayo Foundation for Medical Education and Research, Rochester, MN (US)

(72) Inventors: Allan B. Dietz, Chatfield, MN (US); Michael P. Gustafson, Rochester, MN (US); Greg W. Butler, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 267 days.

(21) Appl. No.: 16/235,392

(22) Filed: Dec. 28, 2018

(65) Prior Publication Data

US 2019/0209617 A1    Jul. 11, 2019

Related U.S. Application Data

(63) Continuation of application No. 14/957,914, filed on Dec. 3, 2015, now Pat. No. 10,166,258, which is a continuation of application No. 13/119,350, filed as application No. PCT/US2009/057170 on Sep. 16, 2009, now abandoned.

(60) Provisional application No. 61/097,490, filed on Sep. 16, 2008.

(51) Int. Cl.
| | | |
|---|---|---|
| *A61K 39/00* | (2006.01) | |
| *C12N 5/00* | (2006.01) | |
| *A61K 35/19* | (2015.01) | |
| *C12N 5/078* | (2010.01) | |
| *C12N 5/0775* | (2010.01) | |
| *C12N 5/09* | (2010.01) | |

(52) U.S. Cl.
CPC ............ *A61K 35/19* (2013.01); *C12N 5/0037* (2013.01); *C12N 5/0644* (2013.01); *C12N 5/0662* (2013.01); *C12N 5/0693* (2013.01); *C12N 2500/90* (2013.01)

(58) Field of Classification Search
None
See application file for complete search history.

(56) References Cited

U.S. PATENT DOCUMENTS

| | | |
|---|---|---|
| 5,185,160 A | 2/1993 | Chao |
| 5,198,357 A | 3/1993 | Holmovist et al. |
| 5,292,362 A | 3/1994 | Bass et al. |
| 5,756,686 A | 5/1998 | Heldin et al. |
| 5,834,418 A | 11/1998 | Brazeau et al. |
| 7,335,508 B2 | 2/2008 | Yayon et al. |
| 8,361,796 B2 | 1/2013 | Menasche et al. |
| 8,501,170 B2 | 8/2013 | Rebulla et al. |
| 10,166,258 B2 | 1/2019 | Dietz et al. |
| 2004/0151709 A1 | 8/2004 | Gorrochategui Barrueta et al. |
| 2005/0214277 A1 | 9/2005 | Schaufler |
| 2006/0014266 A1 | 1/2006 | Tomasevic et al. |
| 2007/0184029 A1 | 8/2007 | Mishra |
| 2009/0023211 A1 | 1/2009 | Persson et al. |
| 2009/0305401 A1 | 12/2009 | Strunk et al. |
| 2010/0120144 A1 | 5/2010 | Mishra |
| 2011/0123498 A1 | 5/2011 | Westenfelder |
| 2012/0156306 A1 | 6/2012 | Weissman et al. |
| 2013/0195959 A1 | 8/2013 | Patel |
| 2014/0335195 A1 | 11/2014 | Houze et al. |
| 2015/0329820 A1 | 11/2015 | Dietz |
| 2016/0074481 A1 | 3/2016 | Burnouf et al. |

FOREIGN PATENT DOCUMENTS

| | | |
|---|---|---|
| EP | 2 733 200 A1 | 5/2014 |
| WO | 89/10398 A1 | 11/1989 |
| WO | 95/15763 A1 | 6/1995 |
| WO | 2005/065419 A2 | 7/2005 |
| WO | 2006/137778 A1 | 12/2006 |
| WO | 2008/034803 A1 | 3/2008 |
| WO | 2008/110570 A1 | 9/2008 |
| WO | 2009/144718 A1 | 12/2009 |
| WO | 2010/017216 A2 | 2/2010 |
| WO | 2010/033605 A2 | 3/2010 |
| WO | 2013/113024 A1 | 8/2013 |
| WO | 2016/139340 A1 | 9/2016 |
| WO | 2016/193591 A1 | 12/2016 |

OTHER PUBLICATIONS

Extended European Search Report, EP Appln. No. 19181191.8, dated Nov. 26, 2019.
Y. Hara et al., "Platelets as a Source of Growth-Promoting Factors for Tumor Cells," Cancer Research, (1980), pp. 1212-1216, XP055275304.
Ogawa et al, "Production of macromolecular activators of phagocytosis by lysed platelets," Thrombosis Res., 97:297-306 (2000).
Piccirillo et al, "Brain tumour stem cells: possibilities of new therapeutic strategies," Expert Opin. on Biol. Ther., 7(8):1129-1136 (2007).
Proulx et al.,"Optimization of culture conditions for porcine corneal endothelial cells," Mol Vis., 13:524-533, Apr. 3, 2007.
Rauch et al., "Laternative to the Use of Fetal Bovine Serum: Human Platelet Lysates as a Serum Substitute in Cell Culture Media" Division of Physiology, Innsbruck Medical University, Innsbruck, Austria; Central Institute of Blood Transfusion and Immunology, University Hospital, Innsbruck Austria, (2011).

(Continued)

*Primary Examiner* — Michail A Belyavskyi
(74) *Attorney, Agent, or Firm* — Merchant & Gould P.C.

(57) ABSTRACT

This document provides methods and materials relating to platelet lysates. For example, methods and materials for using platelet lysate compositions to grow adult stem cells, to differentiate adult stem cells, to grow primary cell cultures, to grow tumor stem cells, and to identify effective growth factors are provided.

11 Claims, 39 Drawing Sheets

(56) References Cited

OTHER PUBLICATIONS

Reddoch et al., "Hemostatic Function of Apheresis Platelets Stored at 4C and 22C," Shock, vol. 41, Supplement 1, pp. 54-61 (2014).
Reply Brief of Maco Pharma in the opposition of EP2334785, dated Oct. 20, 2017.
Ruben et al., "Platelet lysate consisting of a natural repair proteome supports human mesenchymal stem cell proliferation and chromosomal stability," Cell Transplan., 20(6):797-811 (2011).
Schallmoser et al.,"Generation of a pool of human platelet lysate and efficient use in cell culture," Methods Mol Biol., 946:349-62, 2013.
Sell et al,"Incorporating platelet-rich plasma into electrospun scaffolds for tissue engineering applications," Tissue Eng Part A., 17(21-22):2723-2737, Epub Sep. 9, 2011.
Selvaggi et al.,"Development of antibodies to fetal calf serum with arthus-like reactions in human immunodeficiency virus-infected patients given syngeneic lymphocyte infusions," Blood, 89(3):776-779, Feb. 1, 1997.
Singh et al, "Identification of a cancer stem cell in human brain tumors," Cancer Res., 63(18):5821-5828 (2003).
Submission in Reply to notice of opposition of EP2334785 with accompanying auxiliary requests, dated Aug. 9, 2017.
Submission in Response to Summons to Attend Oral Proceedings, EP Appln. No. 09 815 127.7, dated Aug. 10, 2018.
Summons to attend oral proceedings regarding opposition of EP2334785, dated Dec. 20, 2017.
Tekkatte et al.,"Humanized' stem cell culture techniques: the animal serum controversy," Stem Cells Int., 2011:504723, Epub Apr. 3, 2011.
Vogel et al., "Platelet-rich plasma improves expansion of human mesenchymal stem cells and retains differentiation capacity and in vivo bone formation in calcium phosphate ceramics," Platelets; 17(7): 462-469 (Nov. 2006).
Wang et al., "Platelet-induced inhibition of tumor cell growth," Thrombosis Res., 123:324-330 (2008).
Weibrich et al., "Growth factor levels in platelet-rich plasma and correlations with donor age, sex, and platelet count," Craniomaxillofac Surg., 30:97-102 (2002).
Zimmermann et al., "Different preparation methods to obtain platelet components as a source of growth factors for local application," Transfusion, vol. 41, (2001).
Anitua et al., "Autologous preparations rich in growth factors promote proliferation and induce VEGF and HGF production by human tendon cells in culture," Journal of Orthopaedic Research 23 (2005).
Arora, "Cell Culture Media: A Review," Mater Methods, 3:175 (2013).
Attachment to Brief in Opposition of EP2334785 entitled Testing of Platelet Lysate Derived from Platelet Concentrate (Apr. 2, 2009), filed by Maco Pharma, dated Feb. 24, 2017 (french/english version attached).
Barano et al., "Serum-Free Medium Enhances Growth and Differentiation of Cultured Pig Granulosa Cells," Endocrinology, vol. 116, No. 1 (1985).
Barsotti et al.,"Effect of platelet lysate on human cells involved in different phases of wound healing," PLoS One, 8(12):e84753, Dec. 27, 2013.
Bernardo et al, "Optimization of in vitro expansion of human multipotent mesenchymal stromal cells for cell-therapy approaches: further insights in the search for a fetal calf serum substitute," J. of Cell. Phvsiol., 211(1):121-130 (2007) (Abstract only).
Bieback et al., "Clinical Protocols for the Isolation and Expansion of Mesenchymal Stromal Cells," Transfus Med. Hemother (2008).
Brief in Opposition of EP2334785, filed by Maco Pharma, dated Feb. 24, 2017 (french/english version attached).
Brindley et al.,"Peak serum: implications of serum supply for cell therapy manufacturing," Regen Med., 7(1):7-13, Jan. 2012.
Brunner et al.,"Serum-free cell culture: the serum-free media interactive online database," Altex, 27(1):53-62, 2010.
Capelli et al., "Human platelet lysate allows expansion and clinical grade production of mesenchymal stromal cells from small samples of bone marrow aspirates or marrow filter washouts," Bone Marrow Transplantation, 40(8): 785-791 (2007).
Carrancio et al., "Optimization of mesenchymal stem cell expansion procedures by cell separation and culture conditions modification," Experimental Menatology, vol. 36, pp. 1014-1021 (2008).
Chase et al.,"A novel serum-free medium for the expansion of human mesenchymal stem cells," Stem Cell Res Ther., 1(1):8, Apr. 2, 2010.
Communication of a notice of opposition of EP2334785, dated Mar. 13, 2017.
Communication Pursuant to Article 94(3) EPC, regarding EP Appln. No. 15729597.3, dated Jul. 10, 2018.
Communication pursuant to Rule 114(2) EPC, enclosing Third party observations, dated Apr. 25, 2018.
Cowan et al., "Stimulation of human tumor colony formation by platelet lysate," J. Lab. Clin. Med. (1983).
Cryocheck, "Platelet Lysate" Intended use and instruction sheet; 1 page. Printed on Oct. 26, 2014 from Cryopep website at http://cryopep.com/cryocheck-platelet-lysate/.
Dietz et al., "A novel source of viable peripheral blood mononuclear cells from leukoreduction system chambers," Transfusion, 46(12):2083-2089 (2006).
Doucet et al., "Platelet lysates promote mesenchymal stem cell expansion: a safety substitute of animal serum in cell-based therapy applications," J Cell Physiology, 205:228-236 (2005).
Eastment et al., "Platelet Derived Growth Factor(s) for a Hormone-responsive Rat Mammary Tumor Cell Line," Journal of Cullular Physiology, vol. 97, No. 1, (1978).
Edqm, Guide to the preparation, use and quality assurance of Blood Components, European Committee (Partial Agreement) on Blood Transfusion (CD-P-TS), (2015).
"EGM-2 Endothelial Cell Growth Medium-2 BulletKit" Pharma & Biotech, retriefed from the Internet: https://bioscience.lonza.com/lonza_bs/en/Primary-Stem-Cells/p/000000000000185303/EGM-2-Endothelial-Cell-Growth-Medium-2-BulletKit (retrieved on Jul. 4, 2018).
European Search Report in European Application No. 09815127.7, dated Dec. 19, 2012, 12 pages.
European Search Report for Application No. 16170752.6 dated Aug. 29, 2016.
Fan et al., "Glioma stem cells: evidence and limitation," Seminars in Cancer Biol., 17(3):214-218 (2007).
Gruber et al., "Platelet-released supernatants increase migration and proliferation, and decrease osteogenic differentiation of bone marrow-derived mesenchymal progenitor cells under in vitro conditions," Platelets, 15(I):29-35 (2004).
Ho et al., "The Behavior of Human Mesenchymal Stern Cells in 3D Fibrin Clots: Dependence on Fibrinogen Concentration and Clot Structure," Tissue Engineering, 12(6):1587-1595 (2006).
Hoffbauer et al., "Human platelet lysate is a a feasible candidate to replace fetal calf serum as medium supplement for blood vascular and lymphatic endothelial cells," International Society for Cellular Therapy, (2017).
Ihm et al.,"Effects of mixed leukocyte reaction, hydrocortisone and cyclosporine on expression of leukocyte adhesion molecules by endothelial and mesangial cells," J Korean Med Sci., 11(6):495-500, Dec. 1996.
International Preliminary Report on Patentability in International Application No. PCTUS2009057170, dated Mar. 31, 2011, 8 pages.
International Search Report (partial) dated Jul. 31, 2015 for corresponding PCT Patent Application No. PCT/US2015/030834, 5 pages.
Intetnational Search Report (partial) dated Oct. 19, 2015 for corresponding PCT Patent Application No. PCT/US2015/030834, 20 pages.
International Search Report and Written Opinion in International Application No. PCT/US2009/057170, dated May 10, 2010, 12 pages.
Janetzko et al., "Fully automated processing of buffy-coat-derived pooled platelet concentrates," Transfusion, vol. 44 (2004).

(56) References Cited

OTHER PUBLICATIONS

Janowska-Wieczorek., et al, "Enhancing effect of platelet-derived microvesicles on the invasive potential of breast cancer cells," Transfusion, 46:1199-1209 (Jul. 2006).

Janowska-Wieczorek, et al., "Microvesicles derived from activated platelets induce metastasis and angiogenesis in lung cancer," Int. J. Cancer, 113: 752-760 (2005).

Jung et al.,"Ex vivo expansion of human mesenchymal stem cells in defined serum-free media," Stem Cells Int., 2012:123030, 21 pgs, May 7, 2012.

Kitange et al., "Recent advances in the molecular genetics of primary gliomas," Curr Opin Oncol., 15(3):197-203 (2003).

Kocaoemer et al., "Human AB Serum and Thrombin-Activated Platelet-Rich Plasma are Suitable Alternatives to Fetal Calf Serum for the Expansion of Mesenchymal Stem Cells from Adipose Tissue," Stem Cells (2007).

Labitzke et al.,"A serum-free medium formulation supporting growth of human umbilical cord vein endothelial cells in long-term cultivation," Cytotechnology, 35(2):87-92, Mar. 2001.

Lange et al., "Platelet lysate for rapid expansion of human mesenchymal stromal cells," Cellular Therapy and Transplantation, 1(2):6 pages (2008).

Lee et al., "Tumor stem cells derived from glioblastomas cultured in bFGF and EGF more closely mirror the phenotype and genotype of primary tumors than do serum-cultured cell lines," Cancer Cell, 9:391-403 (2006).

Lindroos et al.,"Differential gene expression in adipose stem cells cultured in allogeneic human serum versus fetal bovine serum," Tissue Eng Part A., 16(7):2281-2294, Jul. 2010.

Lucarelli et al., "Platelet-derived growth factors enhanceproliferation of human stromal stem cells," Biomaterials, 24(18):3095-3100 (2003).

Macopharma, "Testing of platelet lysate derived from platelet concentrate" MacoProductions (Apr. 2, 2009).

Marquez-Curtis et al., "Microvesicles Derived from Activated Platelets Enhance the Invasive Potential of Breast Cancer Cells," Blood (ASH Annual Meeting Abstracts); 104: Abstract 3904 (2004).

Martineau et al., "Effects of calcium and thrombin on growth factor release from platelet concentrates: kinetics and regulation of endothelial cell proliferation," Biomaterials; 25(18):4489-4502 (2004).

Mojica-Henshaw et al, "Serum-converted platelet lysate can substitute for fetal bovine serum in human mesenchymal stromal cell cultures," Cyrotherapy (2013), 15, pp. 1458-1468.

Naaijkens et al.,"Human platelet lysate as a fetal bovine serum substitute improves human adipose-derived stromal cell culture for future cardiac repair applications," Cell Tissue Res., 348(1):119-130, Epub Mar. 7, 2012.

A

NSC Media    HCTL #3 Method    10% FBS

B

C

|  | CD133 | Nestin | SOX2 | CD45 | CD34 | CD90 | CD105 | HLA Class I | HLA Class II |
|---|---|---|---|---|---|---|---|---|---|
| NSC Media | 0.51% | +++ | +++ | - | ++ | +++ | - | +++ | ++ |
| HCTL#3 | 15.58% | +++ | ++ | - | ++ | +++ | + | +++ | + |
| 10% FBS | 0.45% | +++ | ++ | - | + | +++ | ++ | ++ | - |

D

| | |
|---|---|
| Neural stem cell media | 73- 83,XXXX.add(1)(p22)x2,inv(3)(p23q26)x2,- 4,add(4)(p12),-5,+7,+7,add(9)(p13)x2,10,-10,-14,-14,-16,-16,-17,-17,-22,- 22[cp20] |
| HCTL #3 media | 72- 82,XXXX,add(1)(p22)x2,2,inv(3)(p23q32)x2,1,- 4,add(4)(p12),-5,+7,+7,add(9)(p13)x2,10,-10,-14,-14,-16,-16,-17,-17,-19,-22,-22,+0-2mar[cp20] |
| DMEM/10% FBS | 69- 75,XXXX,add(1)(p22)x2,2,inv(3)(p23q32)x2,1,-4,-5,-6,+7,+7,add(9)(p13)x2,10,-10,-11,-12,-14,-14,-15,-16,-16,-17,-17,-19,-22,-22,+0- 1mar[cp20] |

| Tumor | Size | Conditions | 30x106/60 days | CD133% | Cytogenetics |
|---|---|---|---|---|---|
| GBM2617-05 | 1.7 | NSC/PL | N/N | 21.2/0.12 | |
| GBM2617-06 | ?2 | NSC/PL | Y/Y | 30/1 | AB/AB |
| GBM083007 | ?1 | NSC/PL/FBS | N/Y/N | 0.5/15.6/0.5 | AB/AB/AB |
| GBM091207 | ?1 | NSC/PL/FBS | N/Y/N | 3.3/38/2.3 | AB/AB/AB |
| GBM2617-07 | 2.4 | NSC/PL/FBS | N/N/N | ND | ND |
| GBM2617-11 | 1.5 | NSC/PL/FBS | N/N/N | ND | AB |
| GBM2617-12 | 4.2 | NSC/PL/FBS | N/N/N | ND | |
| | | | | | |
| GBM101 | 2.1 | NSC/PL/FBS | N/N/N | ND | ND |
| GBM102 | 2.2 | NSC/PL/FBS | Y/N/N | ND | ND |
| GBM103 CUSA | 2.7 | NSC/PL/FBS | N/Y/N | <1% each | AB/AB/AB |
| GBM106 | 2.2 | NSC/PL/FBS | N/Y/N | 14.1/.33/0 | AB/AB/AB |
| GBM108 | 0.9 | NSC/PL/FBS | N/N/N | ND/4.0/0 | AB/AB/AB |
| GBM109 CUSA | 3.2 | NSC/PL/FBS | N/N/N | ND | ND |
| GBM110 | 0.4 | NSC/PL/FBS | N/Y/N | 14.8/0.2 | (TBD) |
| GBM111 CUSA | 3.0 | NSC/PL/FBS | N/Y/N | 5.3/4.7/0 | AB/AB/AB |
| GBM112 | 1.2 | NSC/PL/FBS | N/N/N | ND | ND |

HCTL 7/16 meet vaccine criteria = 44%
NSC 2/16 meet vaccine criteria = 13%
FBS 0/15 meet vaccine criteria = 0%

An additional two cell lines grow in PL (2617-05 and GBM108) but did not meet criteria.

Tissue is essentially cut into fourths, 1 for RNA and 3 for culture conditions

General observations:

NSC: neurospheres, a couple of semiadherent
PL: monolayer and semiadherent, 1 neurosphere
FBS: monolayer General phenotypic analysis
CD90+/CD45-/CD34lo/HLA ABC+/HLA DR-

FIG. 24A

GBM103

| GBM103 | CD133 | Nestin | SOX2 | GFAP | β-III Tub | MBP | CD45 | CD34 | CD90 | CD105 | Class 2 | Class 1 |
|---|---|---|---|---|---|---|---|---|---|---|---|---|
| PL | | ++ | + | ++ | ++ | - | - | - | +++ | - | - | +++ |
| NSC | | +++ | ++ | ++ | ++ | - | - | - | +++ | - | - | +++ |
| FBS | | ++ | + | + | ++ | - | - | - | +++ | - | - | +++ |

| GBM103 | |
|---|---|
| PL | 74-83,XXYY,add(1)(q32),add(2)(q21)x2,-4-4,der(l0)t(7;10)(p11.2,q22)x2,+11,-12,del(13)(q12q14)x2,-14,-14,-15,-16,-16,add(16)(p13.1)x2,der(17)add(17)p(11.2)del(17)(q11.2q21)x2,-19,-19,+0-2mar[cp20] |
| NSC | 64-68,XXY,+Y,-4,-5,der(10)t(7;10)(p11.2;q22),inv(12)(p11.2q15)x2,del(13)(q12q14 x2,-14,die(14;14)(p13;p13),-15,-16,+17,der(17)add(17)p11.2),del(17)(q11.2q21)x2,-18,+19,-20,+21,+0-2mar[cp20] |
| FBS | 61-73,XXY,+Y,+3,-4-6,+7,+8+10,der(10)t(7;10)p11.2;q22)x2,-11,inv(12)(p11.2q15)x2,+13,del(13)(q12q14)x2,-14,-16,der(17)add(17)(p11.2)del(17)(q11.2q21),-18,+20,i(21)(q10),-22,+0-2mar[cp20] |

GBM110; SPORE # 3406

NSC media    DMEM/10% FBS    HCTL media

| GBM110 | CD133 | Nestin | Sox2 | CD45 | CD34 | CD90 | CD105 | Class 1 |
|---|---|---|---|---|---|---|---|---|
| NSC | <1.0% | + | + | - | + | +++ | - | +++ |
| HCTL | <1.0% | + | - | - | + | +++ | - | +++ |
| FBS | <1.0% | + | - | - | + | +++ | - | +++ |

| GBM110 | Karyotype |
|---|---|
| NSC media | 75-84,XXXX,-X,-X,del(1)(q12),-5,-5,-6,+7,+7,+add(7),(q11.2)x2,t(7;18)(p13;p11.2)x2,-8,-10,-10,del(11)(p11.2p13)x2,-12,-13,-13,-14,-14,-15,-15,der(15;21)(q10;q10),i(15)(q10),i(16)(q10),-17,-17,-19,-19,-21,+22,+22,+der(22)t(1;22)(q21;q13),+0-2mar[cp18]/125-153,idemx2[cp2] |
| HCTL media | 62-84,XXXX,-1,-2,-2,-3,-4,-5,-5,-6,+7,+7,+7,+add(7)(q11.2)x2,t(7;18)(p13;p11.2)x2,-8,-8,-10,-10,del(11),(p11.2p13)x2,-13,-13,-14,-14,-15,-15,-16,-17,-17,-18,-18,-19,+0-3mar[cp20] |
| 10% FBS | 73-83,XXXX,-X,-X,-2,-4,-4,inv(4),(q27q35);-5,del(5)(p11),der(5;15)(q10;q10),-6,+7,+7,+add(7)(q11.2)x2,t(7;18)(p13;p11.2)x2,-10,-10,del(11)(p11.2p13)x2,-13,-13,-14,-14,-15,-15,der(15;21)(q10;q10),i(15)(q10),i(16)(q10),-17,-17,-19,-19,+0-3mar[cp16]/141,idemx2,-i(15)[cp2]/46,XX[2] |

GBM111; SPORE # 3407

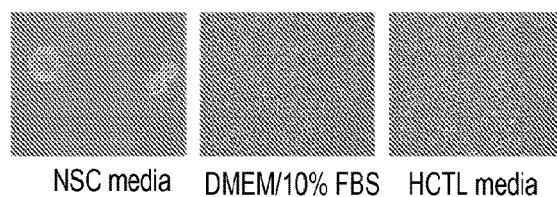

NSC media    DMEM/10% FBS    HCTL media

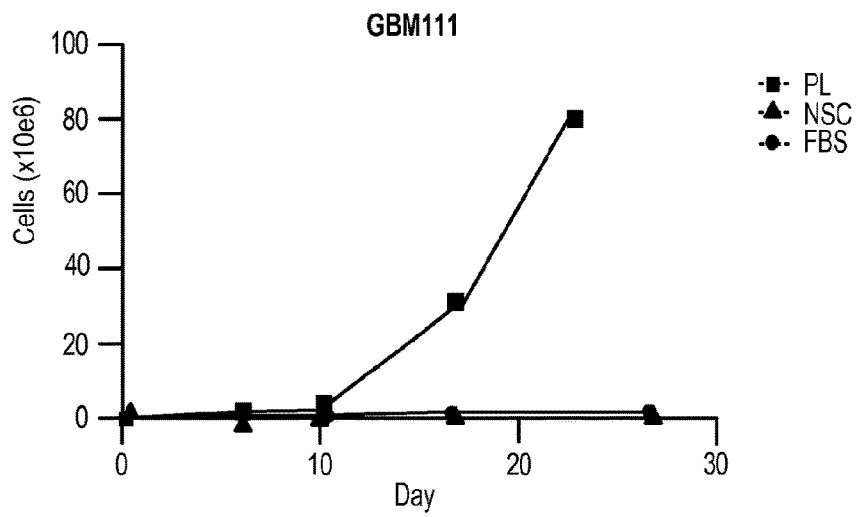

| GBM111 | CD133 | Nestin | SOX2 | GFAP | β-III Tub | MBP | CD45 | CD34 | CD90 | CD105 | Class 2 | Class 1 |
|---|---|---|---|---|---|---|---|---|---|---|---|---|
| PL | 4.79 | + | - | ++ | + | - | - | - | +++ | - | - | +++ |
| NSC | 5.82 | + | - | ++ | + | - | - | - | +++ | - | - | +++ |
| FBS | 0.01 | + | - | + | + | - | - | - | +++ | - | - | +++ |

| GBM111 | Karyotype |
|---|---|
| NSC media | 43-45,XY,t(1;19)(p34.3;q13.3),+7,-9,-10,inv(12)(p13q11),-13,-14,-17,+20,add(21)(p11.2),+1-3mar[cp4]/42-46,sl,t(3;6)(p21;p23)[cp4]/84-86,sdl1x2[cp3]/ 82-89,XXYY,t(1;19)x2,add(5)(p13),+7,+7,-9,-9,-10,inv(12)x2,-13,-13,-14,-14,+20,+20,add(21)(p11.2)x2,+1-2mar[cp9] |
| HCTL media | 46,XY,t(1;19)(p34.3;q13.3),t(3;6)(p21;p23),+7,-10,inv(12)(p13q11),-13,-14,+20,add(21)(p11.2),+1-2mar[cp6]/84-92,idemx2[cp5]/82-88,XXYY,t(;19)x2,-2,-4,-4,add(5)(p13),+7,+7,-9,-9,-10,inv(12)x2,-13,-13,-14,-14,+20,+20,-21,add(21)x2,+2-3mar[cp9] |
| 10% FBS | 54-64,XXY,add(X)(p22.1),+1,add(1)(p13),-3,-4,der(4)t(4;7)(q21;p13),+7,-8,i(8)(q10),-10,-11,psu die(11;15)(p15;p11.2),-12,-13,-14,-16,-17,-18,-18,+20,+21,add(21)(p11.2),-22,+1-4mar[cp20] |

FIG. 24E

COMPOSITIONS CONTAINING PLATELET CONTENTS

This application is a Continuation of U.S. application Ser. No. 14/957,914, filed Dec. 3, 2015, now U.S. Pat. No. 10,166,258, issued Jan. 1, 2019, which is a Continuation of U.S. Ser. No. 13/119,350, filed Mar. 16, 2011, which is a National Stage Application of PCT/US2009/057170, filed Sep. 16, 2009, which claims benefit of U.S. Ser. No. 61/097,490, filed Sep. 16, 2008 and which applications are incorporated herein by reference. To the extent appropriate, a claim of priority is made to each of the above disclosed applications.

BACKGROUND

1. Technical Field

This document relates to methods and materials involved in making and using growth factors, chemokines, and molecules responsible for growing, differentiating, or maintaining undifferentiated cells from normal human platelets (e.g., platelet lysates). For example, this document relates to methods and materials for manufacturing from platelets or platelet preparations (e.g., platelet apheresis preparations) those factors used to grow stem cells (e.g., adult stem cells) rapidly, to maintain them in an undifferentiated form, as an additive to media to differentiate stem cells (e.g., adult stem cells) in combination with other factors, to grow primary cell cultures (e.g., tumor cells and tumor cell lines), and to grow tumor cells with stem cell properties. This document also relates to methods and materials that can be used to identify, isolate, enrich, or optimize combinations of effective growth factors using platelets as a source material. In addition, the document relates to platelet plasma culture supplements and compositions containing platelet contents.

2. Background Information

Cell culture is involved in much of modern biology, drug discovery, and therapy. For example, primary tumor cells can be cultured to obtain an antigen source that can be used in anti-tumor vaccines. Two general methods are used to culture primary brain tumor cells. Traditionally, cells are grown in minimal media supplemented with fetal bovine serum. Cells grown in this way can exhibit limited applicability as an effective antigen source because they often exhibit characteristics of differentiated glial cell subtypes with a reduced ability to recapitulate the original tumor in vivo. Alternatively, cells can be grown in an enriched media supplemented with growth factors, EGF, and FGF. Cells grown in this environment can form neurospheres and can contain populations of tumor stem cells, which more closely recapitulate the phenotypic characteristics of the primary tumor. Although these cells can have reduced proliferative capacities, they are typically less differentiated, more tumorigenic, and more antigenic than cells grown in fetal bovine serum (Lee et al., *Cancer Cell.*, 9:391-403 (2006)). These approaches do not appear to generate primary tumor cultures with high efficiencies and do not appear to allow for the growth of cultures fast enough for many applications. While these methods can be used to generate cell cultures from malignant gliomas, these protocols typically include materials and methods not suitable for clinical use.

SUMMARY

This document provides methods and materials relating to the collection and use of molecules and growth factors found in platelets (e.g., platelet lysates or "PL") or media containing platelets (e.g., a supernatant or filtrate from a platelet preparation such as a platelet apheresis preparation). For example, this document relates to methods and materials for making and using compositions containing platelet contents (e.g., platelet lysates and/or supernatants or filtrates from platelet-containing media). The compositions containing platelet contents provided herein can be used to promote enhanced growth of cells (e.g., normal adult progenitor cells, stem cells, and precursor cells). Examples of such cells include, without limitation, mesenchymal stromal cells, endothelial precursor cells, fibroblasts, and epithelial cells. The compositions containing platelet contents provided herein also can be used to enhance differentiation of progenitor cells, stem cells, and precursor cells into functional subtypes efficiently. In addition, the compositions containing platelet contents provided herein can be used to promote enhanced growth of undifferentiated stem cells such as tumor stem-like cells and adult mesenchymal stromal cells or to maintain cells as a mixture of stem cells and differentiated cells such as that found in primary tumor cultures and tumor cell lines. In some cases, the compositions containing platelet contents provided herein can be used to generate primary cell cultures (e.g., tumor cell lines) efficiently. As described herein, the compositions containing platelet contents provided herein (e.g., platelet lysates, supernatants from platelet-containing media, and filtrates from platelet-containing media) can be used to obtain superior growth kinetics when culturing cells (e.g., progenitor cells and tumor stem-like cells) as compared to cultures using supplementation from human serum, fetal bovine serum, or serum-free media with recombinant growth factor supplementation. The compositions containing platelet contents provided herein also can be manufactured in a manner that is acceptable for clinical use (e.g., meets current good manufacturing practice regulations).

This document also provides platelet plasma culture supplements and cell culture methods and materials for using platelet plasma culture supplements. The term "platelet plasma culture supplement" as used herein refers to a composition that contains (a) plasma (e.g., human plasma) and (b) platelet content that is in the form of a platelet lysate that contained greater than $3 \times 10^8$ platelets per mL (e.g., greater than $4 \times 10^8$ platelets per mL, greater than $5 \times 10^8$ platelets per mL, greater than $6 \times 10^8$ platelets per mL, greater than $7 \times 10^8$ platelets per mL, greater than $8 \times 10^8$ platelets per mL, greater than $9 \times 10^8$ platelets per mL, or greater than $1 \times 10^9$ platelets per mL) before lysis or a medium that contained greater than $3 \times 10^8$ platelets per mL (e.g., greater than $4 \times 10^8$ platelets per mL, greater than $5 \times 10^8$ platelets per mL, greater than $6 \times 10^8$ platelets per mL, greater than $7 \times 10^8$ platelets per mL, greater than $8 \times 10^8$ platelets per mL, greater than $9 \times 10^8$ platelets per mL, or greater than $1 \times 10^9$ platelets per mL) before the platelets were removed. Such a medium can be a supernatant or filtrate obtained from a platelet preparation such as a platelet apheresis preparation or a large scale platelet isolation preparation. In some case, such supernatants or filtrates can be obtained from outdated platelet preparations (e.g., outdated platelet apheresis preparations). Outdated platelet preparations can be platelet preparations (e.g., platelet apheresis preparations) that have been obtained from a live human and stored between 20° C. and 24° C. for more than four days (e.g., more than five, more than six, seven, eight, nine, ten, 11, 12, 15, or more days). Typically, it takes 1-2 liters of blood having a platelet count of 150,000/mm$^3$ to produce one unit of platelets having about $3 \times 10^{11}$ platelets. Any volume of a preparation containing platelets at the above concentrations can be used. For example, 30 mL (e.g., two 15-mL tubes) 50 mL, 100 mL, 500 mL, or an entire unit of platelets can be used to obtain a platelet lysate or a medium (e.g., plasma) that contained greater than $3 \times 10^8$ platelets per mL.

A platelet plasma culture supplement provided herein can have the ability to establish glioma cultures. For example, minimal essential medium having 5 percent of a platelet plasma culture supplement provided herein can be capable of establishing, from newly diagnosed human glioblastoma multiforme biopsy tissue, human glioma cultures having greater than $3 \times 10^7$ cells within 60 days at 37° C. (in a humidified incubator with 5% $CO_2$) with a success rate that is greater than 30 percent (e.g., greater than 35, 40, 45, 50, 55, 60, 65, or more percent). This success rate is based on the number of different newly diagnosed human glioblastoma multiforme biopsy tissue samples (i.e., samples for different humans) that can be used to establish a glioma culture, as opposed to the number of attempts using a single human's glioblastoma multiforme biopsy tissue sample multiple times.

The methods and materials provided herein can be used to grow adult stem cells rapidly, to differentiate stem cells (e.g., adult stem cells), to grow primary cell cultures (e.g., tumor cell lines), to grow tumor stem-like cells, and to identify effective growth factors. For example, the methods and materials provided herein can allow clinicians or medical personnel to develop patient-specific autologous cancer vaccines, while following FDA guidelines. Tumor cells such as malignant glioma cells grown using the methods and materials provided herein can maintain many aspects of neural tumor stem cell phenotypes and can be enriched in tumor-specific antigens desired for recognition of host immune responses. The growth kinetics of cells grown using the methods and materials provided herein can allow clinicians to manufacture sufficient cellular material for multiple vaccinations in a short time frame dictated by current standard therapeutic regimens. Thus, the methods and materials provided herein can provide additional options for the expansion and use of patient specific tumor material for cell therapy.

Another importance of cell culture is the growing use of cells as drugs. In particular, stem cells (both adult and fetal) can be used in regenerative medicine. In such cases, speed of cell growth, fidelity of culture genetics, and clinical applicability can be involved in the success of the cell based therapies.

In general, one aspect of this documents features a platelet lysate composition comprising, or consisting essentially of, a filtrate from a lysed platelet preparation passed through a 0.45 µm or smaller filter. The lysed platelet preparation can be a lysed apheresis platelet preparation. The filter can be a 0.45 µm filter. The filter can be a 0.2 µm filter. The filtrate can be from the lysed platelet preparation being passed through a 0.45 µm filter and a 0.2 µm filter. The lysed platelet preparation can comprise supernatant from centrifugation of lysed platelets. The lysed platelets can be platelets lysed via a freeze/thaw cycle. The lysed platelets can be platelets lysed via at least two freeze/thaw cycles. The centrifugation can comprise a force between 2000×g and 4000×g for between 15 and 45 minutes. The centrifugation can comprise a force of about 3000×g for about 30 minutes. The platelet lysate composition can comprise greater than 200 µg of VEGF polypeptide per mL. Culturing $1.4 \times 10^6$ mesenchymal stem cells with media containing about five percent of the platelet lysate composition can result in greater than $1.4 \times 10^7$ cells after three days. The mesenchymal stem cells can be adipose derived cells.

In another aspect, this document features a platelet lysate composition produced by filtering a lysed platelet preparation through a 0.45 µm or smaller filter. The lysed platelet preparation can be a lysed apheresis platelet preparation. The filter can be a 0.45 µm filter. The filter can be a 0.2 µm filter. The platelet lysate composition can be produced by filtering the lysed platelet preparation through a 0.45 µm filter and a 0.2 µm filter. The lysed platelet preparation can comprise supernatant from centrifugation of lysed platelets. The lysed platelets can be platelets lysed via a freeze/thaw cycle. The lysed platelets can be platelets lysed via at least two freeze/thaw cycles. The centrifugation can comprise a force between 2000×g and 4000×g for between 15 and 45 minutes. The centrifugation can comprise a force of about 3000×g for about 30 minutes.

In another aspect, this document features a method for making a platelet lysate composition. The method comprises, or consists essentially of, filtering a lysed platelet preparation through a 0.45 µm or smaller filter. The lysed platelet preparation can be a lysed apheresis platelet preparation. The filter can be a 0.45 µm filter. The filter can be a 0.2 µm filter. The method can comprise filtering the lysed platelet preparation through a 0.45 µm filter and a 0.2 µm filter. The lysed platelet preparation can comprise supernatant from centrifugation of lysed platelets. The lysed platelets can be platelets lysed via a freeze/thaw cycle. The lysed platelets can be platelets lysed via at least two freeze/thaw cycles. The centrifugation can comprise a force between 2000×g and 4000×g for between 15 and 45 minutes. The centrifugation can comprise a force of about 3000×g for about 30 minutes.

In another aspect, this document features a method for making a platelet lysate composition. The method comprises, or consists essentially of: (a) lysing platelets via one or more freeze/thaw cycles to obtain lysed platelets, (b) centrifuging the lysed platelets to obtain a supernatant, and (c) filtering the supernatant through a 0.45 µm or smaller filter to obtain a filtrate, wherein the filtrate is the platelet lysate composition. The lysing step can comprise at least two freeze/thaw cycles. The centrifuging step can comprise using a force between 2000×g and 4000×g for between 15 and 45 minutes. The centrifuging step can comprise a force of about 3000×g for about 30 minutes. The filter can be a 0.45 µm filter. The filter can be a 0.2 µm filter. The filtering step can comprise filtering the supernatant through a 0.45 µm filter and a 0.2 µm filter. The platelets can be apheresis platelets.

In another aspect, this document features a method for expanding a cell population comprising, or consisting essentially of, culturing a first population of cells in the presence of medium comprising a platelet lysate composition under conditions wherein the first population of cells is expanded to a second population of cells having more cells than the first population, wherein the platelet lysate composition comprises a filtrate from a lysed platelet preparation passed through a 0.45 µm or smaller filter. The cells can be adult stem cells, primary tumor cells, or tumor stem cells.

In another aspect, this document features a method for differentiating stem cells. The method comprises, or consists essentially of, culturing the stem cells in the presence of differentiating medium comprising a platelet lysate composition under conditions wherein the stem cells differentiate, wherein the platelet lysate composition comprises a filtrate from a lysed platelet preparation passed through a 0.45 μm or smaller filter.

In another aspect, this document features a method for healing a wound. The method comprises, or consists essentially of, contacting the wound with a platelet lysate composition, wherein the platelet lysate composition comprises a filtrate from a lysed platelet preparation passed through a 0.45 μm or smaller filter. The wound can be a cut, fistula, or diabetic ulcer. The contacting step can comprise using a stitch or glue comprising the platelet lysate composition to contact the wound. The contacting step can comprise spraying the platelet lysate composition onto the wound.

In another aspect, this document features a composition containing plasma and platelet contents from a platelet preparation passed through a 0.45 μm or smaller filter. The plasma can be human plasma. The platelet contents can be human platelet contents.

In another aspect, this document features a composition comprising medium (e.g., a minimal essential medium) and a platelet plasma culture supplement. The platelet plasma culture supplement can be a platelet lysate comprising plasma. The platelet plasma culture supplement can be a filtrate obtained from filtering a platelet apheresis preparation comprising plasma. The platelet apheresis preparation can be a platelet apheresis preparation collected from a human over three days earlier. The platelet apheresis preparation can be a platelet apheresis preparation collected from a human over five days earlier. The platelet apheresis preparation can be a platelet apheresis preparation collected from a human over six days earlier. The platelet plasma culture supplement can be a supernatant obtained from spinning a platelet apheresis preparation comprising plasma. The platelet apheresis preparation can be a platelet apheresis preparation collected from a human over ten days earlier.

In another aspect, this document features a method for obtaining a platelet plasma culture supplement comprising removing platelets or platelet debris from a platelet apheresis preparation such that at least some of the plasma within the platelet apheresis preparation is retained, thereby obtaining the platelet plasma culture supplement, wherein the platelet plasma culture supplement comprises the ability to induce differentiation of $1\times10^6$ adult stem cells into at least $1\times10^3$ progenitors of cardiomyocytes, adipocytes, osteoblasts, chondrocytes, myocytes, or nerve cells within 60 days when added to medium at a concentration of 5 percent as a base media with supplementation directed at the desired cell type.

In another aspect, this document features an isolated cell culture comprising MCGBM103 cells cultured in medium comprising a platelet plasma culture supplement.

In another aspect, this document features an isolated cell culture comprising MCGBM106 cells cultured in medium comprising a platelet plasma culture supplement.

In another aspect, this document features an isolated cell culture comprising cells cultured in medium comprising a platelet plasma culture supplement, wherein the cells grow in the medium at a rate that is faster than the rate of control cells cultured in control medium comprising 10 percent fetal bovine serum. The cells and the control cells can be primary tumor cells. The cells and the control cells can be human primary glioma cells. The cells and the control cells can be stem cells. The cells and the control cells can be fibroblast cells. The medium and the control medium can be neurobasal medium or DMEM/F12 medium. $1\times10^5$ of the cells can grow in the medium to more than $1\times10^6$ of the cells faster than $1\times10^5$ of the control cells cultured in the control medium grow to $1\times10^6$ of the control cells. $1\times10^5$ of the cells can grow in the medium to more than $3\times10^7$ of the cells faster than $1\times10^5$ of the control cells cultured in the control medium grow to $3\times10^7$ of the control cells. The cells can be primary glioma cells, and $5\times10^5$ of the cells can grow in the medium to more than $1\times10^7$ of the cells within 30 days. The cells can be primary glioma cells, and $5\times10^5$ of the cells can grow in the medium to more than $1\times10^7$ of the cells within 60 days. The cells can be stem cells, and $1\times10^5$ of the cells can grow in the medium to more than $1\times10^7$ of the cells within 14 days. The cells can be stem cells, and $1\times10^5$ of the cells can grow in the medium to more than $1\times10^7$ of the cells within 20 days. The stem cells can be mesenchymal stem cells. The stem cells can be adipose-derived, mesenchymal stem cells. The cells can grow in the medium at a rate that is 1.5 times faster than the rate of the control cells cultured in the control medium.

In another aspect, this document features an isolated cell culture comprising tumor cells cultured in medium comprising a platelet plasma culture supplement, wherein the cells grow in the medium in a manner that is more genetically stable than when control cells are cultured in control medium comprising 10 percent fetal bovine serum. The tumor cells and the control cells can be primary tumor cells. The tumor cells and the control cells can be human primary glioma cells. The medium and the control medium can be neurobasal medium or DMEM/F12 medium. The tumor cells grown in the medium for four doublings can exhibit less than a five percent change in karyotype as compared to the tumor cells grown in the medium for one doubling. The tumor cells grown in the medium for four doublings can exhibit less than a three percent change in karyotype as compared to the tumor cells grown in the medium for one doubling. The tumor cells grown in the medium for ten doublings can exhibit less than a five percent change in karyotype as compared to the tumor cells grown in the medium for one doubling.

In another aspect, this document features an isolated cell culture comprising stem cells cultured in medium comprising a platelet plasma culture supplement, wherein the stem cells grow in the medium in a manner that is more genetically stable than when control stem cells are cultured in control medium comprising 10 percent fetal bovine serum. The stem cells and the control stem cells can be mesenchymal stem cells. The stem cells and the control stem cells can be adipose-derived, mesenchymal stem cells. The medium and the control medium can be neurobasal medium or DMEM/F12 medium. The stem cells grown in the medium for four doublings can exhibit less than a five percent change in karyotype as compared to the stem cells grown in the medium for one doubling. The stem cells grown in the medium for four doublings can exhibit less than a three percent change in karyotype as compared to the stem cells grown in the medium for one doubling. The stem cells grown in the medium for ten doublings can exhibit less than a five percent change in karyotype as compared to the stem cells grown in the medium for one doubling.

In another aspect, this document features a method for obtaining a platelet plasma culture supplement. The method comprises, or consists essentially of, removing platelets or platelet debris from a platelet apheresis preparation such that at least some of the plasma within the platelet apheresis preparation is retained, thereby obtaining the platelet plasma culture supplement, wherein the platelet plasma culture supplement comprises the ability to induce proliferation of less than $1\times10^6$ adipose-derived, mesenchymal stem cells at passage five into at least $1\times10^8$ cells within 20 days when added to minimal essential medium at a concentration of 5 percent. The platelet plasma culture supplement can comprise the ability to induce proliferation of less than $1\times10^6$ adipose-derived, mesenchymal stem cells at passage five into at least $1\times10^8$ cells within 15 days when added to minimal essential medium at a concentration of 5 percent.

In another aspect, this document features a method for obtaining a platelet plasma culture supplement. The method comprises, or consists essentially of, removing platelets or platelet debris from a platelet apheresis preparation such that at least some of the plasma within the platelet apheresis preparation is retained, thereby obtaining the platelet plasma culture supplement, wherein minimal essential medium having 5 percent of the platelet plasma culture supplement is capable of establishing, from newly diagnosed human glioblastoma multiforme biopsy tissue, human glioma cultures having greater than $3\times10^7$ cells within 60 days at 37° C. with a success rate that is greater than 30 percent. The success rate can be greater than 40 percent.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
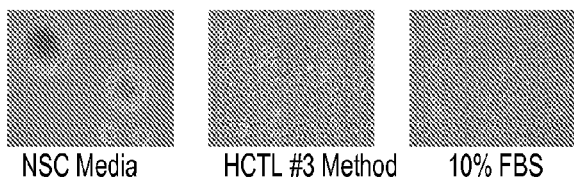
FIG. 1. Autologous primary neurospheres exhibited enhanced growth kinetics and characteristics of tumor stem cells. A. Morphology of a GBM tumor split and grown independently in Neural Stem Cell (NSC) media (neurospheres), HCTL #3 (mostly adherent cells in this particular cell culture; grown using 5% platelet lysate), and DMEM+ 10% FBS (monolayer forming adherent cells). Light phase photomicrographs, 10×. B. Growth kinetics of GBM tumor grown using the three different methods. C. A table listing staining results for neural stem cell and other cell surface markers. Cells were grown on coverslips, and nestin and SOX2 expression was analyzed by indirect immunofluorescence. All other markers were measured by staining cells for each and analyzing them using flow cytometry. +++ indicates >90% positive cells, ++>50%, +>10%, and – indicates <1% positive cells. D. Cytogenetic analysis of GBM083007 grown in the three different cultures. 20 metaphase cells were counted in each analysis.
Figure 1:
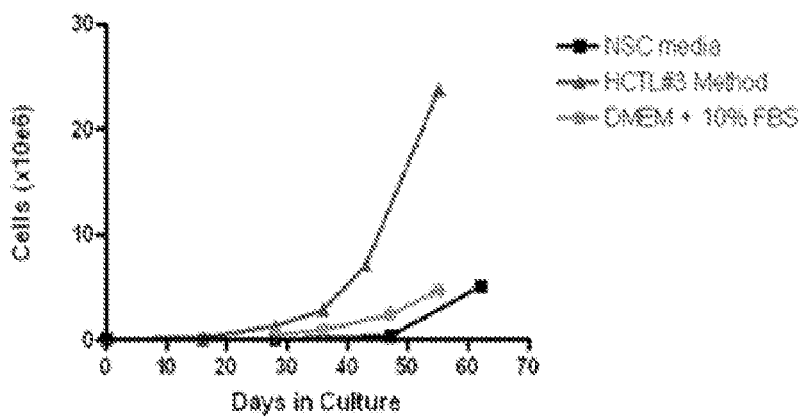

This document provides methods and materials related to compositions containing platelet contents (e.g., platelet lysates and/or supernatants or filtrates from platelet-containing media). For example, this document relates to methods and materials for making and using compositions containing platelet contents. Any appropriate source of platelets can be used to make a composition containing platelet contents. For example, apheresis platelets and platelets derived from normal blood donation can be used as a source of platelets for making a platelet lysate composition, a supernatant or filtrate from a platelet-containing medium, or a platelet plasma culture supplement.

In one embodiment, a composition containing platelet contents (e.g., a platelet lysate) can be obtained as follows. Once obtained, platelets contents can be released using any appropriate method including, without limitation, a single freeze/thaw cycle, repeated (e.g., 2, 3, 4, 5, or more) freeze/thaw cycles, detergent lysis, activation with thrombin, collagen, thromboxane A2, ADP or other factors, and manipulation of ionic strength. In some cases, two freeze/thaw cycles can be used to obtain lysed platelets. Once lysed, the lysed platelet preparation can be centrifuged to obtain a supernatant. In general, the force of centrifugation can be between 2000×g and 5000×g, and the duration can be between 10 minutes and 60 minutes. For example, a lysed platelet preparation can be centrifuged at about 3,000×g for about 30 minutes. Once the supernatant is collected, it can be filtered. For example, the supernatant can be filtered through a 0.45 µm filter, a 0.2 µm filter, or a 0.45 µm filter followed by a 0.2 µm filter. The resulting filtrate can be used as a platelet lysate composition without further processing or can be combined with heparin to form a platelet lysate composition.

A platelet lysate provided herein can be prepared without washing the platelets prior to lysing them. In such cases, the platelet lysate can include plasma and plasma components. For example, a platelet lysate provided herein can include albumin and/or thrombin at about physiologic concentrations. In some cases, a platelet lysate provided herein can include platelet contents prepared from platelets lysed in the presence of plasma or a plasma-like composition.

In another embodiment, a composition containing platelet contents (e.g., a supernatant or filtrate from platelet-containing media) can be obtained as follows. Platelets can be maintained between 2° C. and 42° C. (e.g., between 2° C. and 40° C., between 2° C. and 38° C., between 2° C. and 36° C., between 2° C. and 30° C., between 5° C. and 36° C., between 10° C. and 36° C., between 15° C. and 36° C., between 20° C. and 30° C.) for a period of time (e.g., two, three, four, five, or more days) in the presence of plasma without performing an active step designed to lyse the platelets. For example, a platelet preparation (e.g., outdated platelet preparation) obtained from an apheresis technique can be used without removing the plasma. Once obtained, the platelet preparation can be treated to remove platelets, platelet debris, or platelet ghosts, while obtaining the resulting medium that includes platelet contents and plasma components. For example, this resulting medium can be obtained by centrifugation and/or filtration. Once obtained, the resulting medium can be stored or used as a composition containing platelet contents or a platelet plasma culture supplement as described herein.

The compositions containing platelet contents (e.g., platelet lysate compositions) provided herein can be formulated with any appropriate medium to produce a culture medium having enhanced properties. Examples of media that can supplemented with a composition provided herein include, without limitation, DMEM, RPMI, AIMV, X-VIVO15, and other defined serum free or serum requiring media. Any appropriate amount of a composition containing platelet contents provided herein can be added to a medium. For example, 1, 2, 3, 4, 5, 6, 7, 8, 9, 10, or more percent (e.g., vol/vol) of a medium can be a platelet lysate composition or a platelet plasma culture supplement provided herein. Such supplemented media can be used to promote enhanced growth of cells (e.g., normal adult progenitor cells, stem cells, precursor cells, fibroblasts cells, and mesenchymal stromal cells), to differentiate progenitor cells, stem cells, and precursor cells into functional subtypes efficiently, to promote enhanced growth of tumor stem cells in primary tumor cultures, to establish tumor cell lines, or to generate primary cell cultures (e.g., tumor cell lines) efficiently. As described herein, the compositions containing platelet contents (e.g., platelet lysate compositions) provided herein can be used to obtain superior growth kinetics when culturing cells (e.g., progenitor cells and tumor stem cells) as compared to cultures using supplementation from human serum, fetal bovine serum, or serum-free media with recombinant growth factor supplementation.

The compositions containing platelet contents (e.g., platelet lysate compositions) provided herein can be used to supplement media used to culture cells from any species including, without limitation, humans, monkeys, horses, dogs, cats, rats, or mice.

Any appropriate method can be used to derive differentiated cells from stem cells (e.g., mesenchymal stem cells). For example, differentiated cells can be derived from mesenchymal stem cells by incubating the mesenchymal stem cells with a composition (e.g., culture media) containing one or more factors together with a composition containing platelet contents (e.g., a platelet lysate composition) provided herein. The factors can be any type of factors such as polypeptides, steroids, hormones, and small molecules. Examples of such factors may include, without limitation, dexamethasone, EGF, FGF and BMP4. Stem cells can be incubated with a such compositions for 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 days. In some cases, a composition provided herein and used to promote cell growth or differentiation can be replaced every day or every 2, 3, 4, 5, 6, 7, 8, 9, 10, 11, 12, 13, 14, 15, 16, 17, 18, 19, 20, 21, 22, 23, 24, 25, 30, 35, 40, 45, 50, or more days.

Once stem cells (e.g., mesenchymal stem cells) have been incubated with a composition provided herein or otherwise treated with differentiation factors, the state of differentiation can be monitored to determine whether or not the stem cells differentiated into differentiated cells having a desired phenotype. For example, a sample of cells can be collected and assessed using techniques such as Western blotting, fluorescence-activated cell sorting (FACS), immunostaining, laser confocal microscopy, and reverse transcription polymerase chain reaction (RT-PCR) techniques (e.g., quantitative RT-PCR).

Figure 24B:
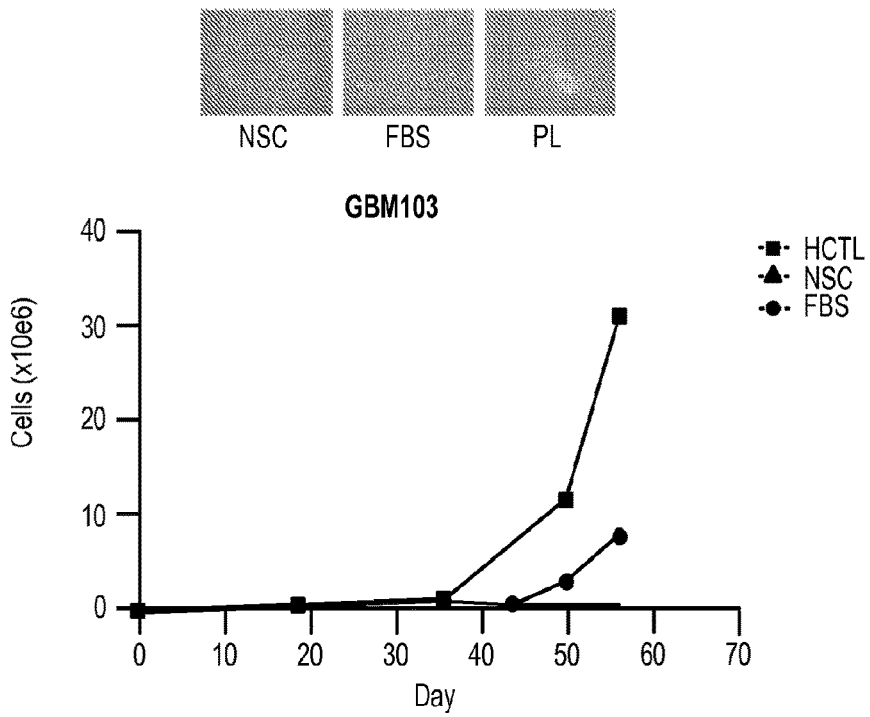
FIG. 24A is a table listing the results from culturing primary tumor cells with the indicated media, and FIGS. 24B, 24C, 24D, and 24E contain data regarding GBM103, GBM106, GBM110, and GBM111 cell cultures, respectively.

This document also provides isolated cell cultures. For example, this document provides isolated primary tumor cell cultures such as a GBM106 cell culture or any other tumor cell culture identified in FIG. 24A. It is noted that the isolated primary tumor cell cultures identified in FIG. 24A can be designated with an "MC" prefix when established using a composition containing platelet contents provided herein. For example, the GBM106 cell culture obtained using a platelet lysate provided herein can be designated as MCGBM106. Likewise, the GBM110 cell culture obtained using a platelet lysate provided herein can be designated as MCGBM110, and so on. An isolated primary tumor cell culture provided herein can be obtained from a human patient and cultured in the presence of medium supplemented with a composition containing platelet contents. For example, a medium containing between 1 percent and 50 percent (e.g., between 1 percent and 45 percent, between 1 percent and 35 percent, between 1 percent and 25 percent, between 1 percent and 15 percent, between 1 percent and 10 percent, between 1 percent and 5 percent, between 5 percent and 50 percent, between 10 percent and 50 percent, between 20 percent and 50 percent, between 3 percent and 10 percent, or between 3 percent and 7 percent) of a platelet plasma culture supplement provided herein can be used to culture human primary glioma cells.

Cells (e.g., primary tumor cells) cultured as described herein can exhibit rapid growth kinetics (FIGS. 1 and 29), higher frequency of cell line establishment (FIGS. 24A-E), and stable genetics (FIG. 1). With reference to FIG. 1, it is noted that the karyotype of cells cultured with the HCTL #3 and the NSC media can be very similar, while the karyotype of the cells cultured with FBS can be different. This was done starting with a single tumor sample. Thus, the FBS cultured cells evolved away from the other two cell lines. The other two cell lines are very similar suggesting that these two reflect the progenitor tumor.

Figure 29:
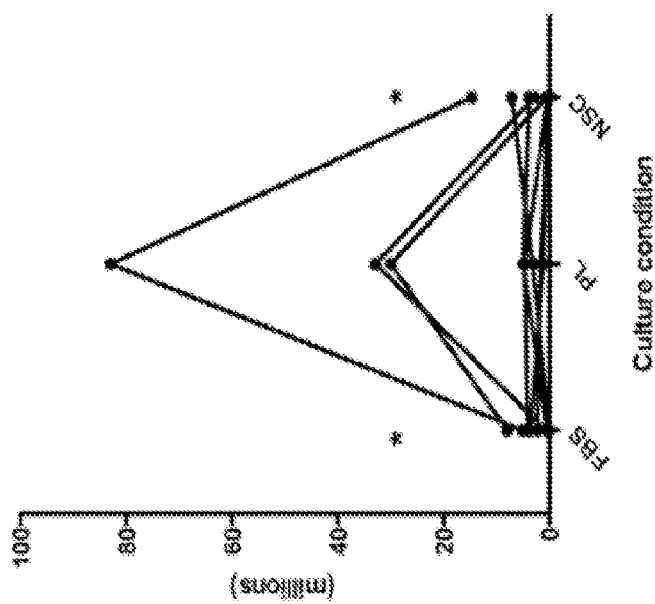
FIG. 29. PL promotes rapid growth of primary GBM cultures. Example growth kinetics of a primary tumor grown in each media supplement (left panel), and total cells obtained after 20-30 days of culture for multiple tumor isolates (right panel). PL was superior in the number of cells grown independent of the individual tumor (p=0.05; n=8).
Figure 29:
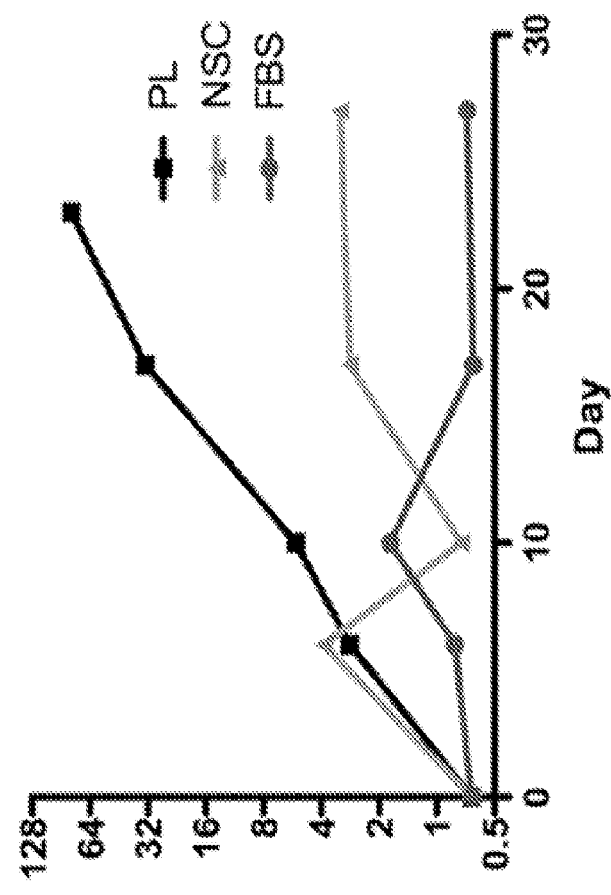

In some cases, primary tumor cells cultured as described herein can exhibit a constant doubling time (FIG. 29). A constant doubling time can indicate that there is no significant lag time in establishing the culture. Thus, there are no other needed factors that require genetic rearrangements/or additives to have the cultures grow.

Primary tumor cells cultured as described herein also can exhibit the presence of cells with progenitor phenotypes. An example of SOX2 and CD133 expression in a primary tumor culture is provided in FIG. 1. SOX2 and CD133 are markers of progenitor cells associated with tumor progenitor cells (tumor stem cells). Primary tumor cells cultured as described herein can be GMP compatible since the supplement (e.g., a composition containing platelet contents such as a platelet plasma culture supplement) can be GMP compatible.

In some cases, primary tumor cells cultured as described herein can be biologically relevant in that many tumors are associated with blood clots. While not being limited to any particular mode of action, a blood clot may act like an in vivo matrix for the collection of platelet supernatants. Thus, a composition containing platelet contents provided herein can mimic the normal biology of the tumor.

The invention will be further described in the following examples, which do not limit the scope of the invention described in the claims.

EXAMPLES

Example 1—Source of Platelets

All donors donating apheresis platelets fulfilled eligibility criteria as defined by AABB Standards for Blood Banks and Transfusion Service and the Food and Drug Administration. Donors were screened using the Uniform Donor History Questionnaire (UDQ) and accompanying educational materials. This questionnaire is a screening document created by a coalition of regulatory, accrediting, and blood collecting institutions consisting of the Food and Drug Administration, Centers for Disease Control and Prevention, Armed Services Blood Program, National Heart Lung and Blood Institute, American Blood Resources Association, AABB, American Red Cross, and America's Blood Centers. Information concerning the UDQ can be found on the World Wide Web at "fda.gov/cber/dhq/dhq.htm."

All apheresis platelet donations were tested with the following infectious disease tests: (1) Serologic test for syphilis; (2) HCV EIA-hepatitis C virus antibody test, (3) HCV NAT-hepatitis C virus nucleic acid test, (4) HbsAg-hepatitis B surface antigen test, (6) Anti-HBc-hepatitis B Core antibody, (7) HIV-1/2 EIA-Human Immunodeficiency Virus 1/2 antibody test with ability to detect HIV 1 subgroup O; (8) HIV NAT-Human Immunodeficiency Virus nucleic acid test, (9) HTLV I/II EIA-Human T-Lymphotrophic Virus Types I/II, (10) WNV NAT-West Nile Virus nucleic acid test, and (8) Anti-*T. cruzi*, (serologic test for Chagas disease) using FDA licensed procedures.

In addition to the above tests, all apheresis platelet products were also tested for bacterial contamination. Twenty-four hours after collection, the product was resuspended, and an 8 mL sample was collected. Four mL of this sample was inoculated into an anaerobic culture bottle, and 4 mL was inoculated into an aerobic bottle. These bottles were then placed into a BacT/ALERT® system (bioMérieux, Durham, N.C., USA) within three hours of inoculation and monitored for $CO_2$ generation for 24 hours. If after 24 hours $CO_2$ production was not detected, the platelet products were released and made available for transfusion. The culture bottles continued to be monitored for the remaining shelf-life of the platelet product (total of five days; three additional days after release).

The platelet products that were released for manufacture of the growth media were collected from donors who fulfill donation criteria, were negative tests for the infectious diseases listed above, and exhibited no evidence of bacterial growth by their expiration date. Products from donors who failed to meet donor criteria, that exhibited positive infectious disease testing, or that produced cultures positive for bacteria were considered biohazardous waste. These products were quarantined and destroyed. They were not released for manufacture of a platelet lysate growth media. FDA tests and guidelines for release can change. However, platelets used for these purposes met FDA tests and guidelines current at the time of production.

Example 2—Preparing Platelet Lysate from Apheresis Platelets

Apheresis platelets were obtained as described in Example 1. The apheresis platelets used were no more than four days past expiration. A single lot of platelet lysate consisted of ten individual apheresis platelet units, and one lot was used at a time to create a platelet lysate product. The processing for clinical grade reagents can be performed in a clean room suite. Ten individual apheresis platelet units were frozen at −70° C. or colder. After being frozen for at least 24 hours, the units were removed from the freezer and allowed to thaw. The units were thawed at room temperature or at refrigerated temperatures. After thawing was complete, each unit was mixed by massaging the bag. Each thawed platelet bag was placed flat (to minimize breakage of tubing) in a supercold freezer (−70° C. or colder) for a second freeze. After the apheresis platelet units were frozen for at least 24 hours for a second freeze, they were removed from the freezer and allowed to thaw. After the second thaw, the platelet product was aseptically transferred to 250 mL conical centrifuge tubes. The tubes were centrifuged for 30 minutes at 3000×g for 30 minutes at room temperature using a Benchtop Centrifuge Sorvall Legend T. The resulting supernatants were transferred to 0.45-micron filter units (Pall Stericup, Catalog Number SCHV U05 RE; East Hills, N.Y. or Nalgene Filter System, Catalog Number 167-0045; Rochester, N.Y.) that were pre-fitted with one or more pre-filters (Glass Microfibre filters GF/B or GF/D used interchangeably; Whatman®, Florham Park, N.J.). The filter unit was connected to a vacuum source and allowed to filter the product. If the product did not filter completely, the unfiltered product was transferred to another filter unit with a pre-filter. The filtrates from all of the 0.45-micron filter units were pooled and filtered through a 0.2-micron filter unit (Pall Stericup, Catalog Number SCHV U05 RE; East Hills, N.Y. or Nalgene Filter System, Catalog Number 567-0020; Rochester, N.Y.) that was pre-fitted with one or more pre-filters (Glass Microfibre filters GF/B or GF/D used interchangeably; Whatman®, Florham Park, N.J.). The filter unit was connected to a vacuum source and allowed to filter the product. If the product did not completely filter, the unfiltered product was transferred to a second filter unit, and the process was repeated as needed. The 0.2-micron filtrates were combined into receiver bottles.

A plasma transfer set was connected to a 60-mL syringe, and the transfer set was spiked into a 2 L blood bag. Using the syringe as a funnel, the filtered lysates from the apheresis platelet units were combined into the 2 L bag. The contents were mixed well. Heparin (1000 U/mL) was added to the filtered platelet lysates to obtain a final concentration of two U/mL.

The lysates were divided into aliquots. The lysates were stored frozen at ≤20° C. or colder.

One of the aliquots containing the platelet lysate was used to perform the following tests to determine whether or not to release the platelet lysate preparation for use:

Aerobic Culture.

One mL of platelet lysate was transferred to a Peds Bactec blood culture bottle (Becton, Dickinson and Company; Sparks, Md.) that was used to test sterility.

Anaerobic Culture.

Eight mL of platelet lysate was transferred to a Bactec Lytic/10 Anaerobic/F bottle (Becton, Dickinson and Company; Sparks, Md.). Briefly, both aerobic and anaerobic bottles are loaded in the BACTEC 9240 instrument (Becton, Dickinson and Company; Sparks, Md.) and monitored every four hours for 14 days. After 14 days, negative cultures are reported out as "No growth at 14 days", positive cultures are subcultured and isolates identified.

Endotoxin Assay.

One mL of platelet lysate was transferred to a sterile endotoxin-free tube that was used to perform an endotoxin assay. Briefly, a 1:50 dilution of Platelet Lysate to Limulus Amebocyte Lysate (LAL) Reagent Water was run on the Endosafe Portable Test System (PTS; Charles River, Wilmington, Mass.). The Endosafe PTS utilizes LAL kinetic chromogenic methodology to measure color intensity directly related to the endotoxin concentration in a sample. Each disposable cartridge contains precise amounts of licensed LAL reagent, chromogenic substrate, and control standard endotoxin. The result obtained from each batch of Platelet Lysate must be <0.500 Endotoxin Units (EU)/mL.

Cell Kinetics.

A batch (≥150 mL) of Platelet Lysate-5% (PL5%) media containing Advanced-MEM (120 mL), GlutaMAX (1.2 mL), Heparin (~0.24 mL), and 5% platelet lysate (6.4 mL) was prepared. A vial of Previously frozen Mesenchymal Stem cells (reference cells) were thawed in a 37° C. waterbath. Once thawed, the cells were placed in a sterile 50 mL tube with about 5 mL of the PL5% media. The tube was spun at 240×g for 5 minutes. The supernatant was removed from the tube, and one mL of the PL5% media was added to the cell pellet. A cell count was performed. The thawed cells were placed in one to two 175 cm$^2$ flasks with 50 mL of PL5% so that each flask contained $1.75 \times 10^5$-$4.38 \times 10^5$ of the thawed cells. The flasks were incubated at 37° C. in a 5 percent $CO_2$ incubator. The cells were passaged using TrypLE™ (Invitrogen Corporation, Carlsbad, Calif.) after the flasks were confluent. The cells were combined, and a cell count performed. A population doubling calculation was performed.

Flow Cytometry.

The cells from the cell kinetic assay were assessed using the following flow cytometry panel:

| Tube # | FITC | PE |
|---|---|---|
| 1 | IgG1 | IGg1 |
| 2 | IgG2 | IgG2 |
| 3 | CD90 | CD73 |
| 4 | CD105 | HLA-DR |
| 5 | CD44 | HLA-ABC |
| 6 | CD45 | CD14 |

Platelet lysates that were sterile, endotoxin-free, grew MSC with the expression profile of CD105, CD90, CD73, HLA-ABC positive and negative for CD14, CD45, and HLA-DR were released for clinical use and assigned an expiration date of two years from production.

Example 3—Culturing Cells with Platelet Lysates

The phenotypic characteristics of GBM cells cultured with media containing platelet lysates were compared to those of GBM cells cultured using NSC media (Neurobasal media (Invitrogen, Grand Island N.Y.); recombinant EGF and FGF (R&D Systems, Minneapolis, Minn.), N2 and B27 supplements (Invitrogen, Grand Island N.Y.), glutamine and penicillin/streptomycin) or DMEM containing 10% FBS. The media containing platelet lysate (HCTL #3) consisted of Neurobasal media supplement with 5% platelet lysate, glutamine, and penicillin/streptomycin. Cells grown in NSC media formed classical neurospheres enriched in tumor stem cells (FIG. 1A). Cells grown in DMEM 10% FBS became adherent and were usually differentiated (FIG. 1A). Cells grown in HCTL #3 resulted in a mixed population of free-floating neurospheres and adherent neuropheres with superior growth kinetics (FIGS. 1A and 1B). Cells cultured in HCTL #3 also exhibited many aspects of neural tumor stem cells and were positive for CD133, nestin, and SOX2 (FIG. 1C). In addition, cells grown in HCTL #3 were cytogenetically abnormal as often seen in primary GBM tumors (FIG. 1D; Kitange et al., Curr. Opin. Oncol., 15(3): 197-203 (2003)).

Figure 24C:
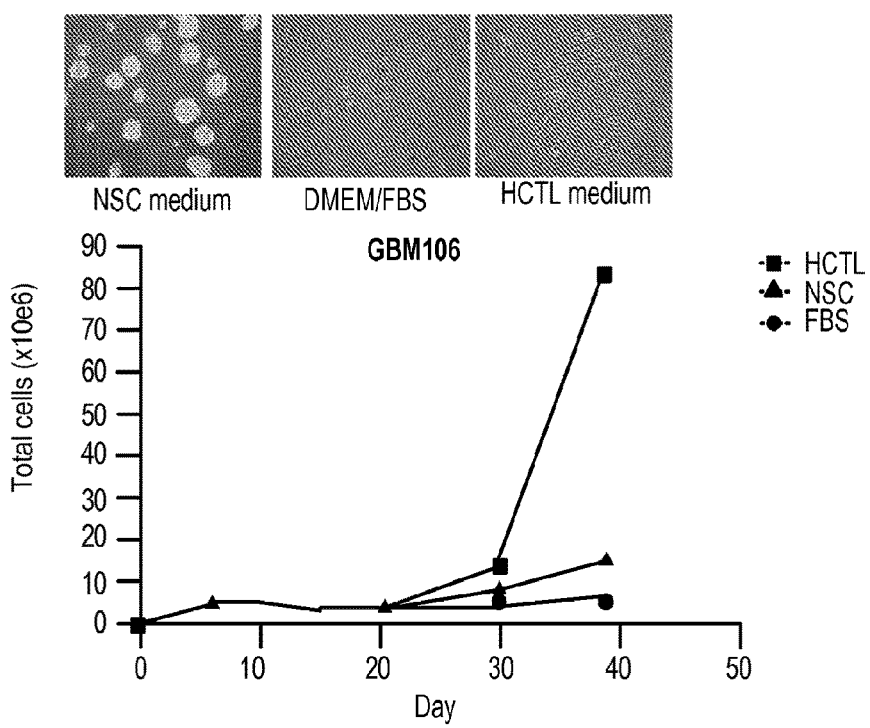
Figure 24D:
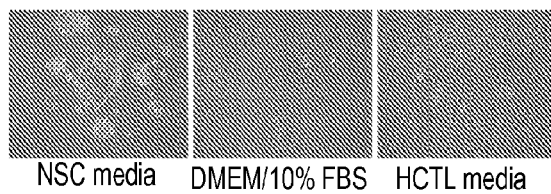
Figure 24D:
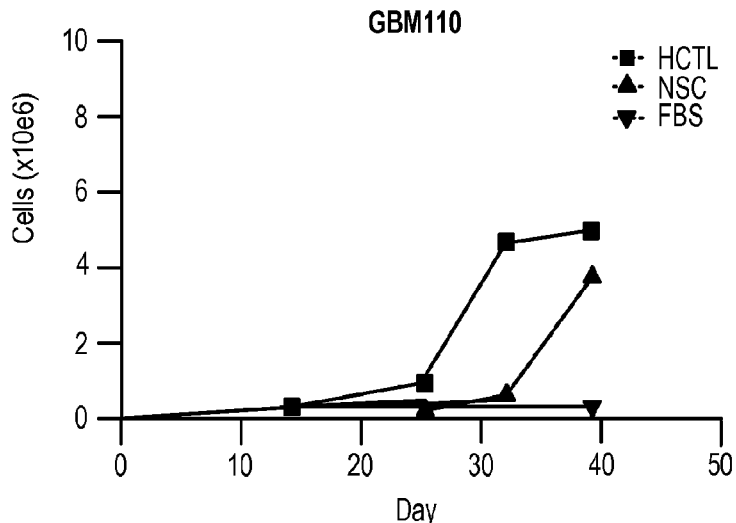
Figure 25:
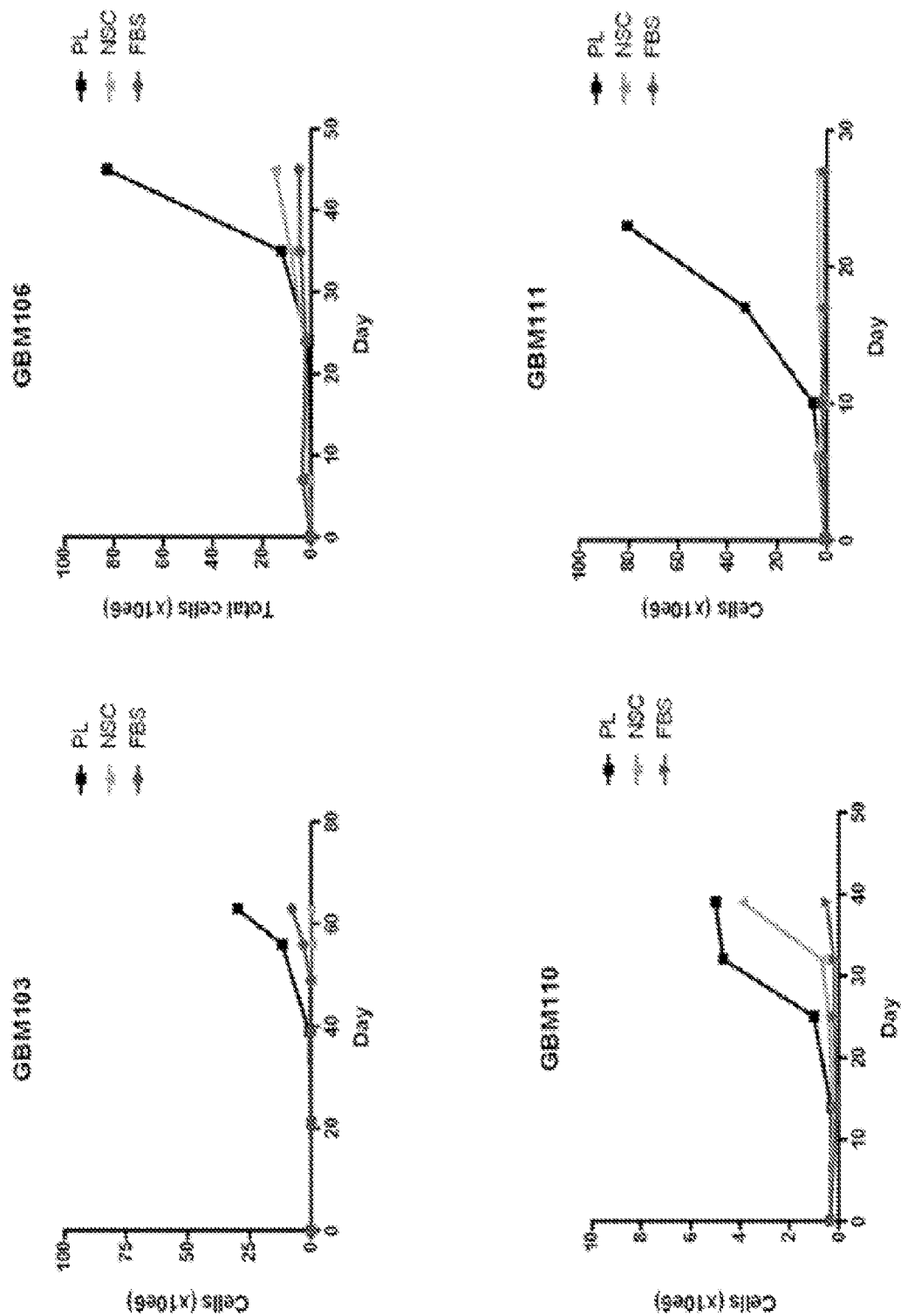
FIG. 25 contains four graphs plotting the number of cells at the indicated day for primary tumor cells grown in PL (AIM-V media supplemented with 5% platelet lysate as per example 2), NSC media (Neurobasal-A media with N2 and B27 supplements and EGF and FGF), or DMEM 10% FBS.
Figure 26:
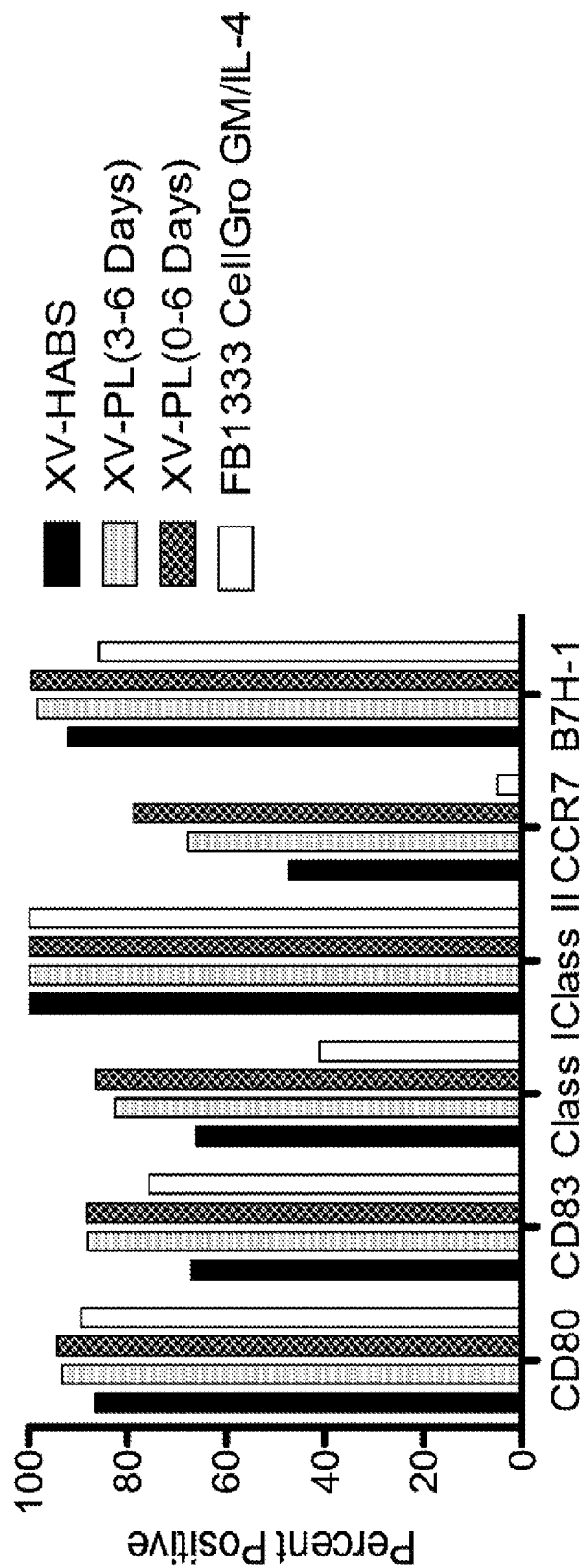
FIG. 26 is a graph plotting the percent positive dendritic cells for the indicated marker of CD14+ monocytes cultured ex-vivo with 1% HABS in X-Vivo 15 media (XV-HABS), 1% platelet lysate-containing X-Vivo 15 media (XV-PL), or CellGro serum free media (no supplementation). All indications contained 2800 IU GM-CSF and 1000 IU IL-4 for the entire course of culture (six days). All conditions had TNF-α and PGE2 added on day three, and the cells were phenotyped on day six. For XV-PL (3-6) the culture was incubated in HABS for the first three days and PL for the last two.

Additional results culturing primary tumor cells are presented in FIGS. 24A-E and 25. These additional results demonstrate that the platelet lysates provided herein can perform better than fetal calf scrum and a defined supplemented media (NSC) for growing primary tumor cells (e.g., gliomas) (FIGS. 24A-E). These results also demonstrate that platelet lysate-containing media can grow tumors in less time (FIG. 25).

Figure 2:
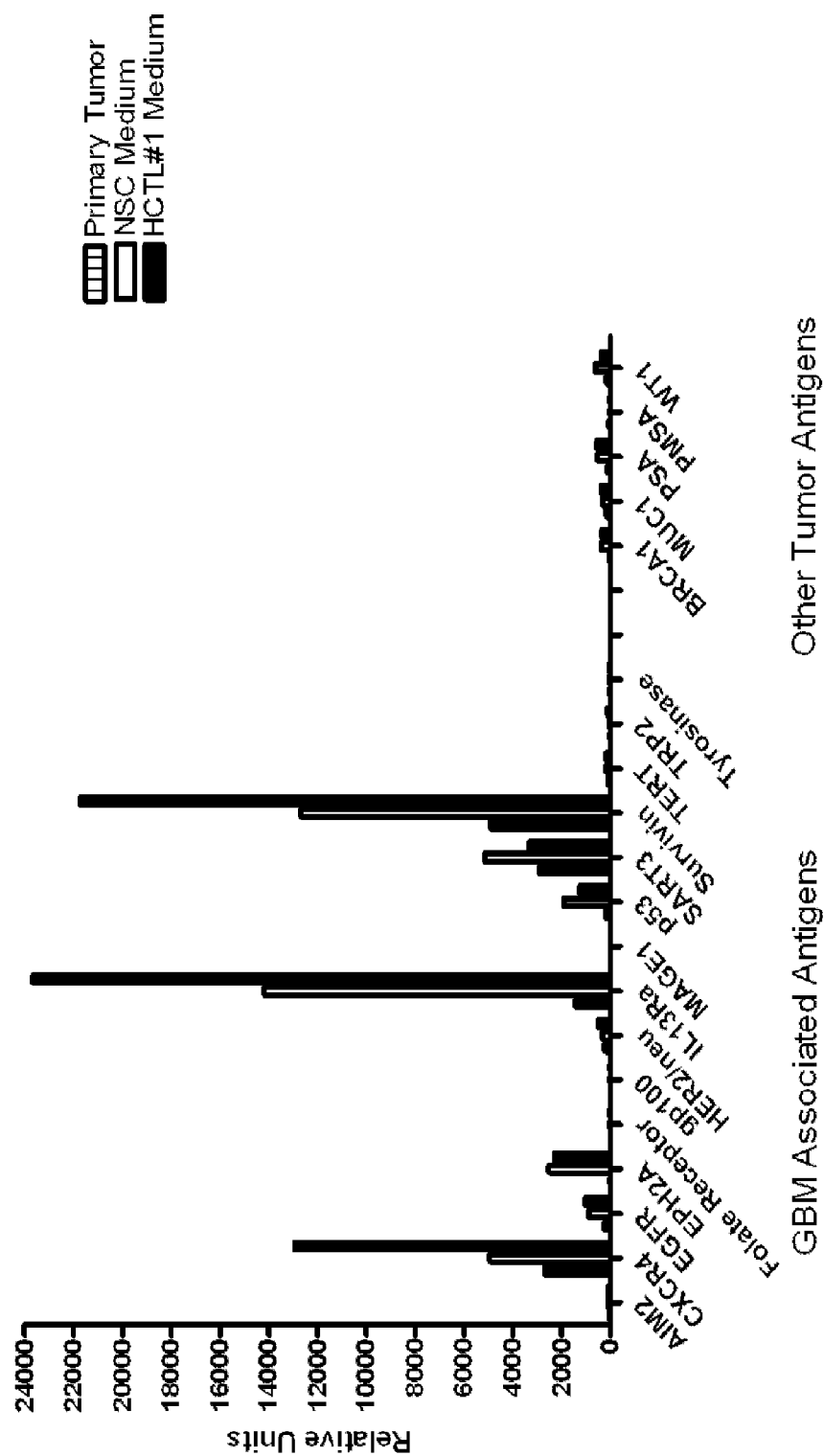
FIG. 2. Identification and monitoring of tumor associated antigens in autologous primary brain tumor cultures. Gene chip analysis was used to determine relative antigen expression in primary tumors (black bars), tumor stem cell cultures obtained using the Fine protocol (Lee et al., *Cancer Cell.*, 9:391-403 (2006)) (open bars; also known as NSC medium, Neural basal medium, neural stem cell medium), and brain tumor cultures using HCTL #1 (filled bars; grown using platelet lysate, and base media was DMEM/F12).

Tumor cells grown in media supplemented with manufactured platelet lysate were enriched for primary GBM-associated tumor antigens that were similar, if not superior, to cells grown in NSC media (FIG. 2). As such, the PL supplemented media allowed for the generation of primary cell cultures from GBM patients that exhibited superior growth kinetics, characteristic tumor genetic rearrangements, populations of neural tumor stem cells, and enrichment in certain tumor antigens. The use of lysates from autologous tumor cultures as antigen for DC immunotherapy offers the advantage of targeting multiple tumor antigens reflective of the patient's antigen profile, eliminating contaminating cells, and providing sufficient antigen for multiple immunizations. Preliminary research in GBM patients demonstrated the consistent ability to generate primary tumor cultures from small portions of resected tumor.

Figure 3:
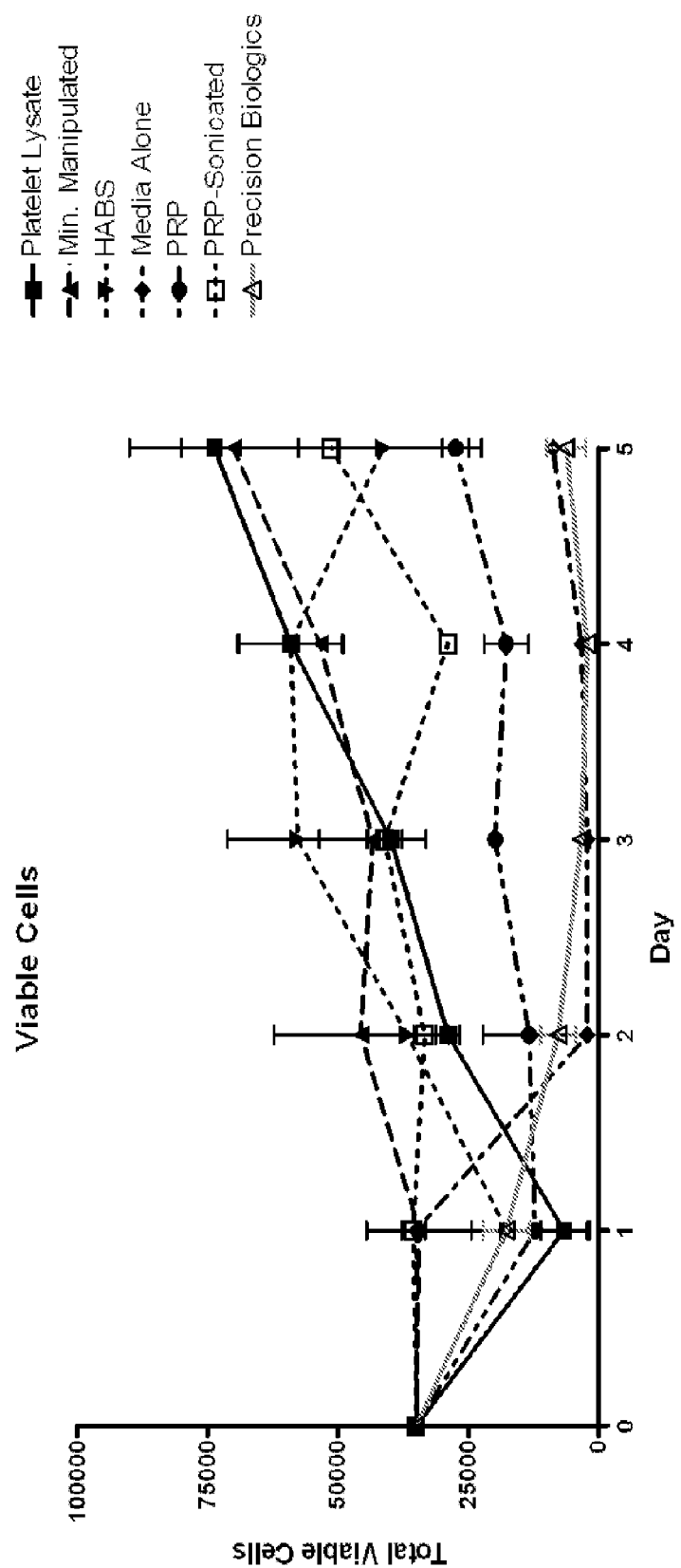
FIG. 3 is a graph plotting the total number of viable GBM cells after one, two, three, four, or five days of being cultured with the media containing the indicated components.
Figure 4:
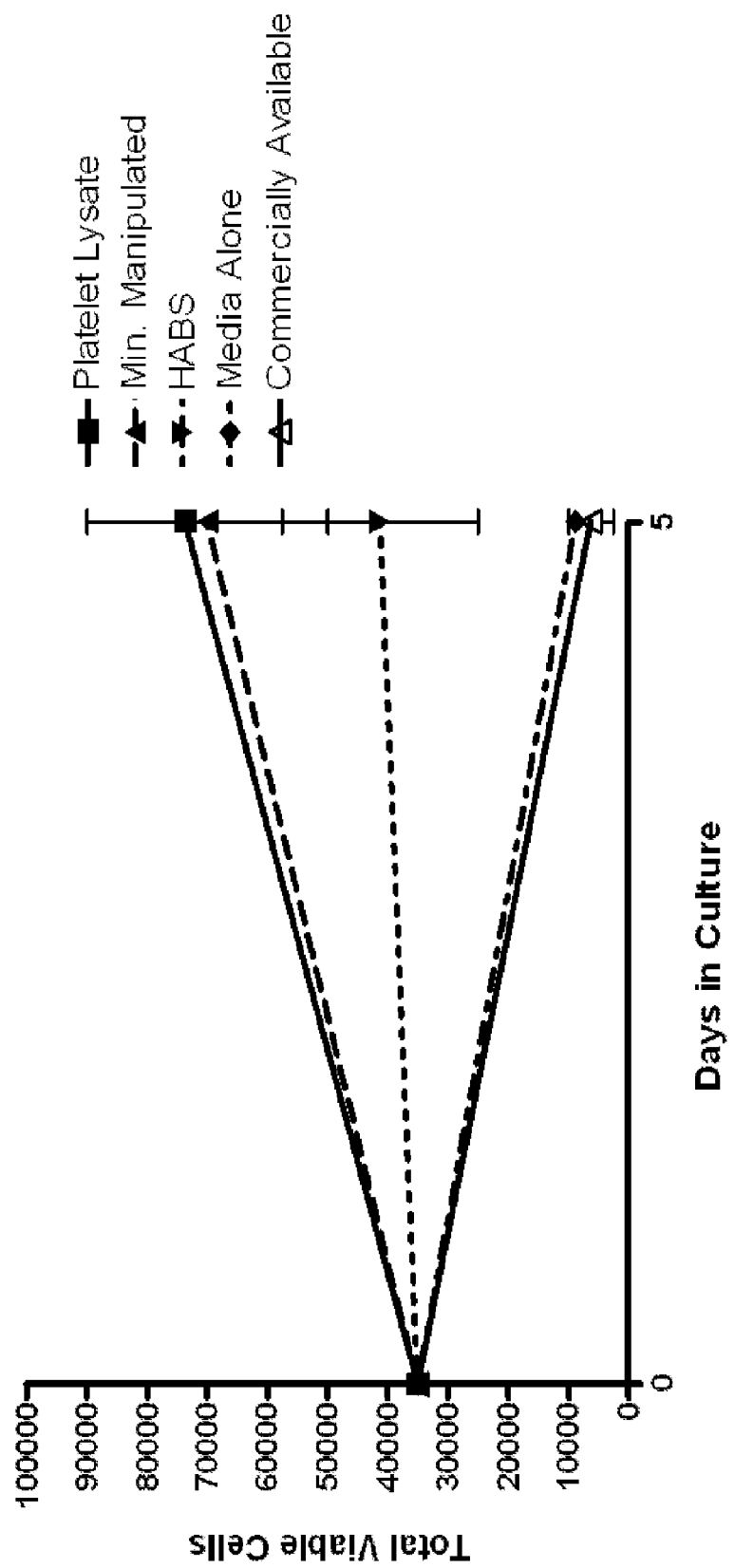
FIG. 4 is a graph plotting the total number of viable GBM cells after five days of being cultured with the indicated media.

Cells cultured from a primary brain tumor were thawed and plated ($3.5 \times 10^4$ cells/well) in one of the following culture media: Neurobasal media (Invitrogen, Grand Island, N.Y.) plus 5% fully manufactured platelet lysate (platelet lysate), Neurobasal media containing 5 percent platelet lysate from a single freeze/thaw cycle without further processing (Min. Manipulated), Neurobasal media containing 5 percent human AB serum (HABS, Sigma, St. Louis, Mo.), Neurobasal media alone, Neurobasal media containing 5 percent platelet rich plasma (PRP), Neurobasal media containing 5 percent platelet rich plasma that was sonicated (PRP-Sonicated), and Neurobasal media containing 5 percent of a commercially available platelet lysate (Cat. No. PNP-10, Lot No. PL14, Precision Biologic, Dartmouth, Nova Scotia). Equal numbers of cells were plated in duplicate for each condition. The cells were cultured for five days, and the total viable number of cells was counted each day (FIG. 3). The results from day 5 are presented in FIG. 4. These results demonstrate that in this experiment, tumor cells grew the best in fully manufactured platelet lysate.

Figure 5:
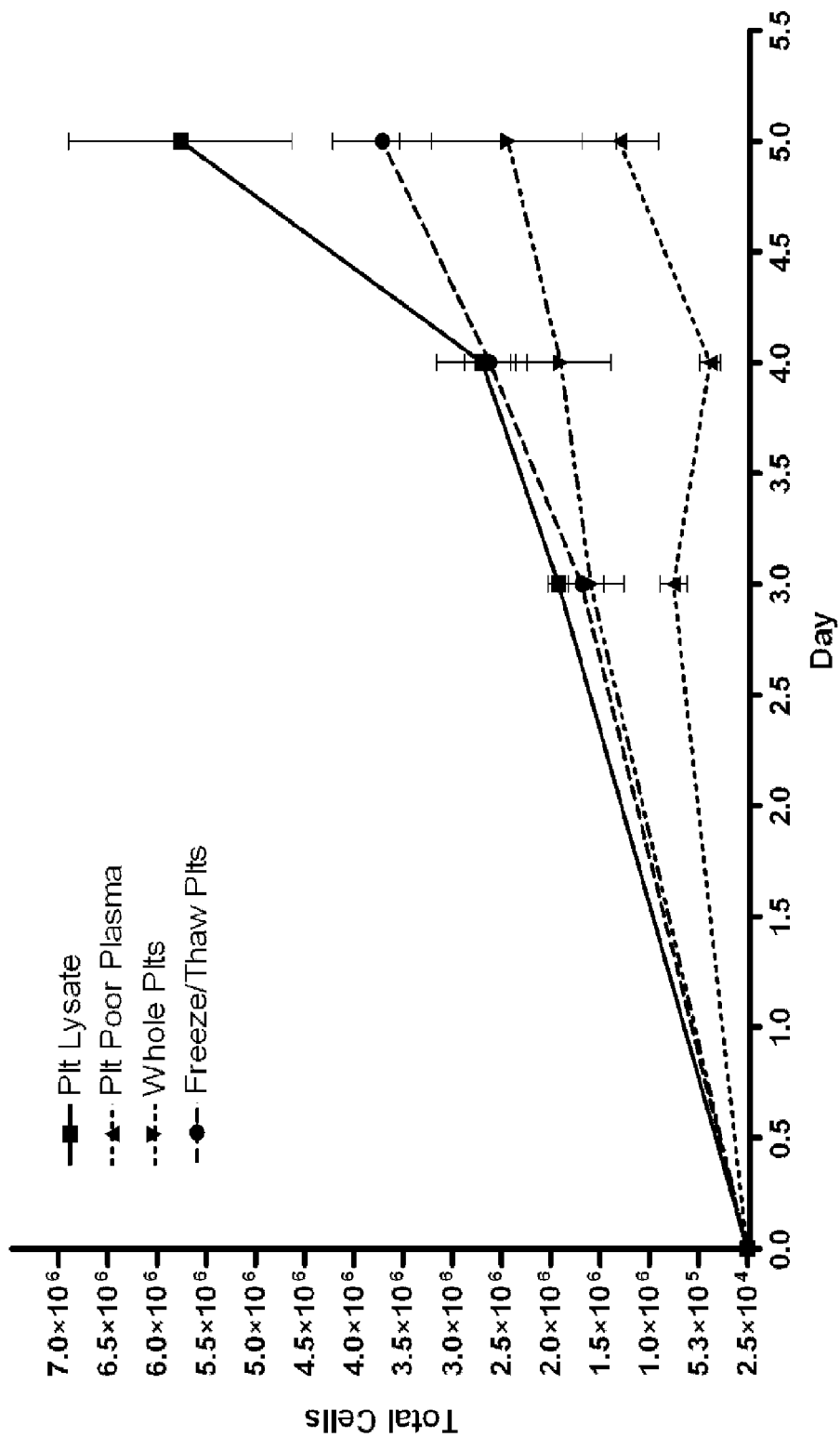
FIG. 5 is a graph plotting the total number of MSCs after three, four, or five days of being cultured with the media containing the indicated components.

MSCs were thawed and grown in Advanced MEM (Invitrogen, Grand Island, N.Y.) plus 5% HCTL manufactured platelet lysate until confluent. The cells were then passaged and split into Advance MEM with the following supplements: 5 percent (vol/vol) of a platelet lysate prepared as described in Example 2, platelet poor plasma (plt. poor plasma), whole platelets (whole plts.), or platelet exposed to two freeze/thaw cycles without further processing (Freeze/thaw plts.). The 5 percent platelet lysate was used as baseline with the others being adjusted to provide an equivalent protein concentration as the 5 percent platelet lysate. The cells were allowed to equilibrate in their specific media for a few days before beginning the experiment. Once prepared, the MSC were plated at $2.5 \times 10^4$ cells/plate into T25 flasks with their appropriate medium. The total number of cells in each of three flasks for each condition was counted on days three, four, and five (FIG. 5). These results demonstrate that MSCs grew the best in HCTL fully manufactured lysate.

Figure 6:
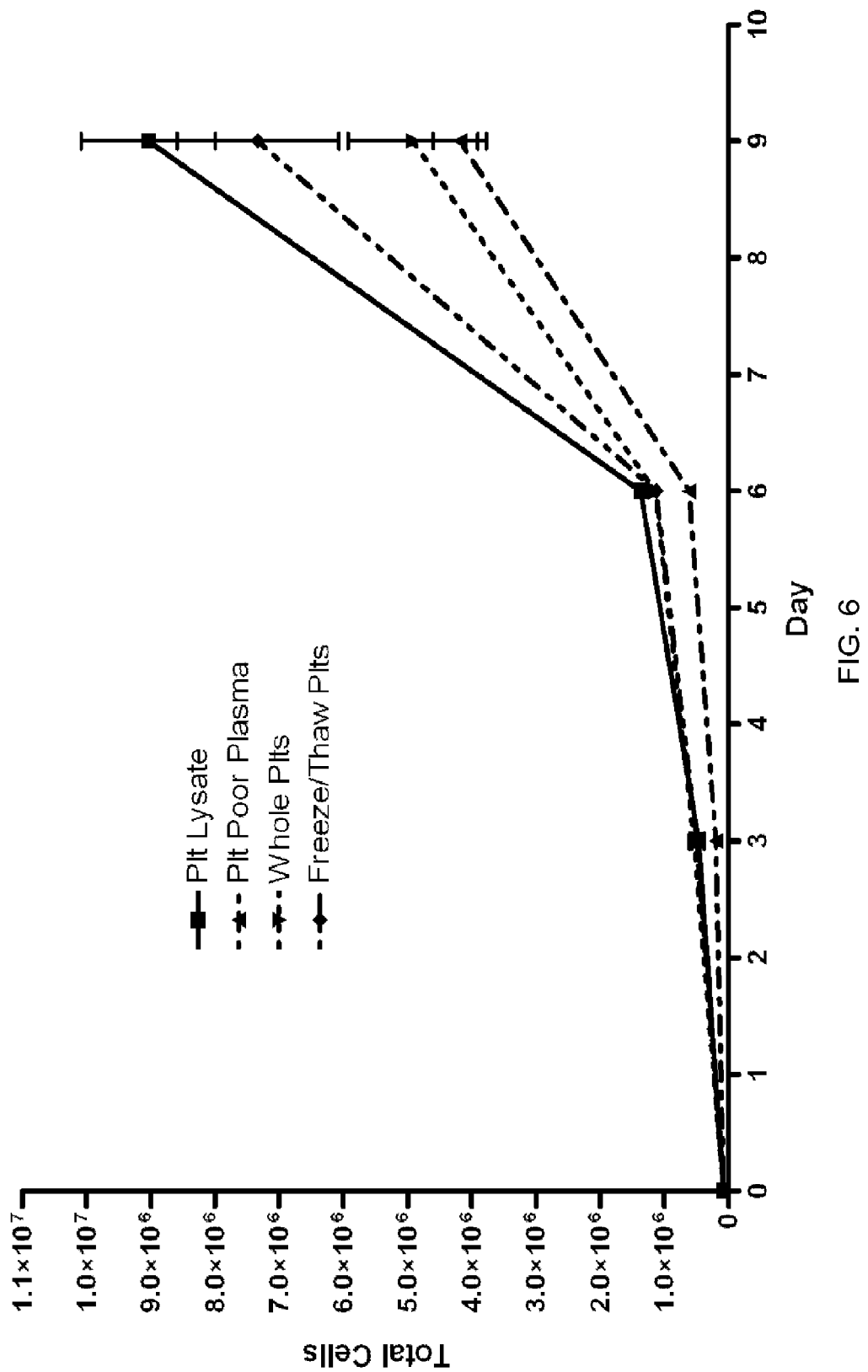
FIG. 6 is a graph plotting the number of GBM cells after three, six, and nine days of being cultured with the Neurobasal Media (Invitrogen, Grand Island, N.Y.) containing the indicated components.

A cell line from a primary tumor was thawed and plated similarly to the MSC growth experiment. Conditioned cells were then plated at $8 \times 10^4$ cells/plate in Neurobasal Media (Grand Island, N.Y.) supplemented with either 5 percent (vol/vol) of a platelet lysate (PL) prepared as described in Example 2, platelet poor plasma (plt poor plasma or PPP), whole platelets (whole plts or WP), or platelet exposed to two freeze/thaw cycles without further processing (Freeze/thaw pits or FT). The 5 percent platelet lysate was used as baseline with the others being adjusted to provide an equivalent protein concentration as the 5 percent platelet lysate. The cells were allowed to equilibrate in their specific media for a few days before beginning the experiment. The total number of cells in each of three flasks for each condition was counted on days three, six, and nine (FIG. 6). These results demonstrate that cells grew better in fully manufactured platelet lysate over 6 days.

Figure 7:
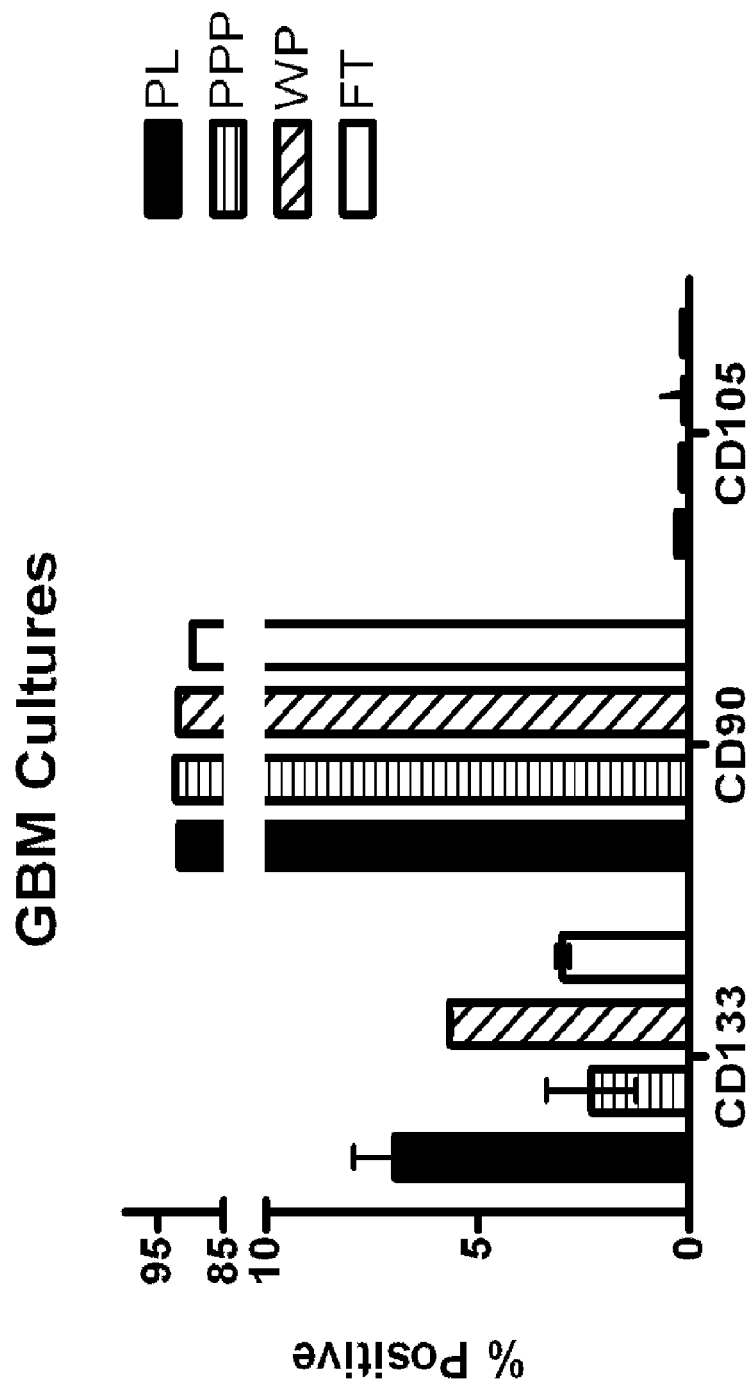
FIG. 7 is a graph plotting the percent of CD133, CD105, and CD90 positive GBM cells after being cultured with the Neural Basal Media containing the indicated components.

On day 5, the cells from each flask for each particular condition type were pooled and analyzed by FACS for CD133 (two tubes were assessed), CD105 (one tube), and CD90 (one tube). The percent of positive cells for each marker was determined (FIG. 7). These results demonstrate that cells grown in fully manufactured platelet lysate were enriched for CD133+ cells. CD133 expression has been documented as a marker for glioma-initiating stem cells (Singh et al., *Cancer Res.*, September 15; 63(18):5821-8 (2003)).

Figure 8:
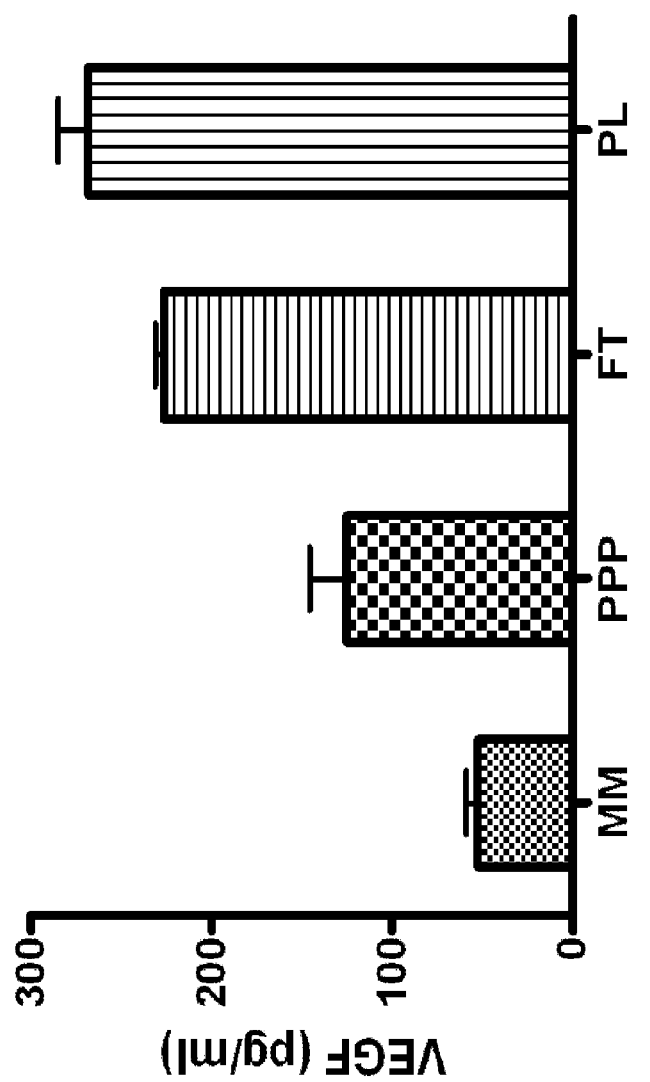
FIG. 8 is a graph plotting the amount of VEGF (pg/mL) present in the indicated preparations. MM=minimally manipulated apheresis platelets from expired donations that were not frozen (3 bags were combined). PPP=Platelet poor plasma, which is a fraction of minimally manipulated apheresis platelets that were spun down at 3000 g for five minutes and then spun at 10,000 g for one minute. FT=freeze/thaw fraction, which is minimally manipulated apheresis platelets that were subjected to two freeze/thaw cycles. PL=platelet lysate prepared as described in Example 2. MM, PPP, FT, and PL were obtained from the same starting material and were stored for over two months at 4° C.

In another experiment, the amount of VEGF (pg/mL) present in various platelet preparations was determined (FIG. 8). The platelet preparations included (1) minimally manipulated (MM) apheresis platelets from expired donations that were not frozen (3 bags were combined), (2) platelet poor plasma (PPP), which was a fraction of minimally manipulated apheresis platelets that were spun down at 3000 g for five minutes and then spun at 10,000 g for one minute, (3) a freeze/thaw fraction (FT), which contained minimally manipulated apheresis platelets that were subjected to two freeze/thaw cycles, (4) platelet lysate (PL) prepared as described in Example 2. The MM, PPP, FT, and PL preparations were obtained from the same starting material and were stored for over two months at 4° C. The PL preparation exhibited the highest level of VEGF (FIG. 8). These results demonstrate that our manufacturing process increases the concentration of this growth factor and is highest at the final step of manufacturing.

Figure 9:
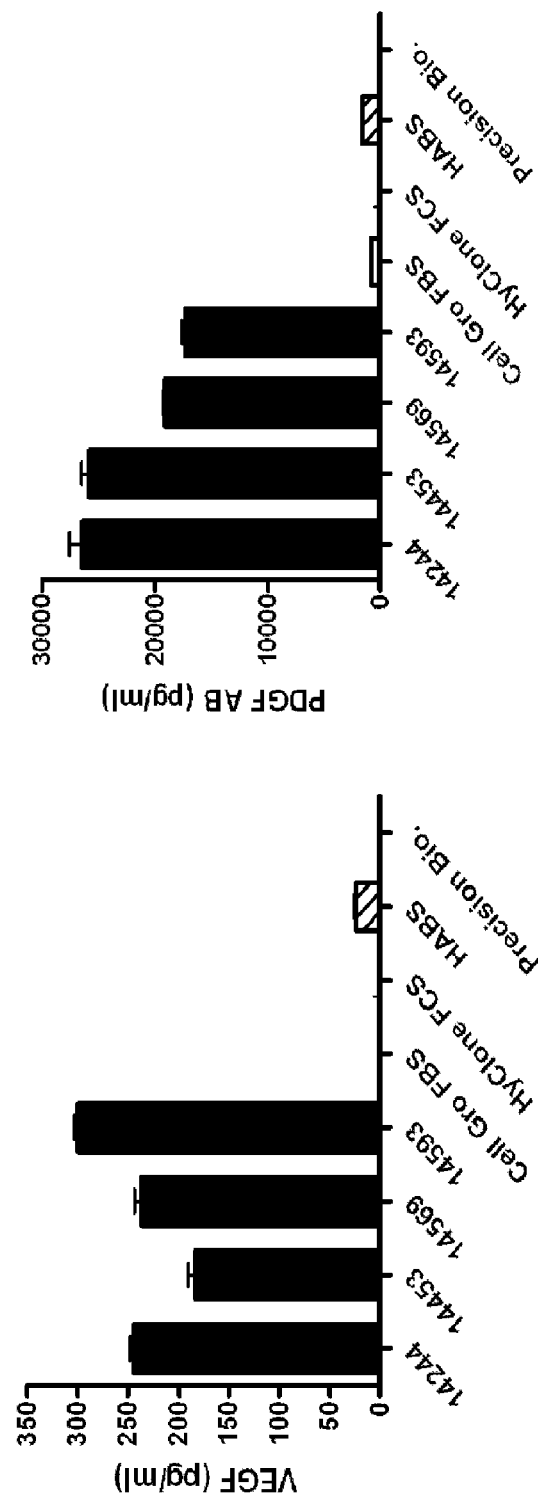
FIG. 9 demonstrates that the levels of growth factors (VEGF and PDGF) are consistent across different lots of manufactured platelet lysates. The levels of these growth factors are significantly higher in the final product preparations versus other growth factor supplements like fetal bovine serum, fetal calf serum, human AB serum, and another commercially available platelet lysate preparation.

Subsequent experiments demonstrate that the levels of VEGF and PDGF are consistent across several different lots of platelet lysate manufactured in the HCTL (14244, 14453, 14569, and 14593) (FIG. 9). In addition, these growth factors are significantly higher on a per volume basis than that of other growth supplements including fetal bovine serum, fetal calf serum, human AB serum, and another commercially available platelet lysate preparation (Cat. No. PNP-10, Lot No. PL14, Precision Biologic, Dartmouth, Nova Scotia).

Figure 35:
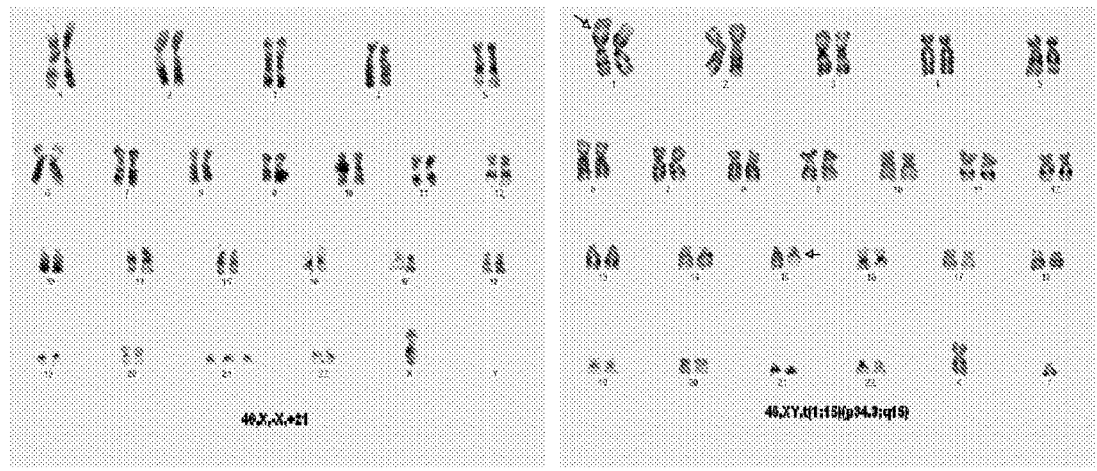
FIG. 35 is contains the karyotype data for two mesenchymal stromal cell isolates cultured in either 10% FBS or 5% PL.
Figure 35:
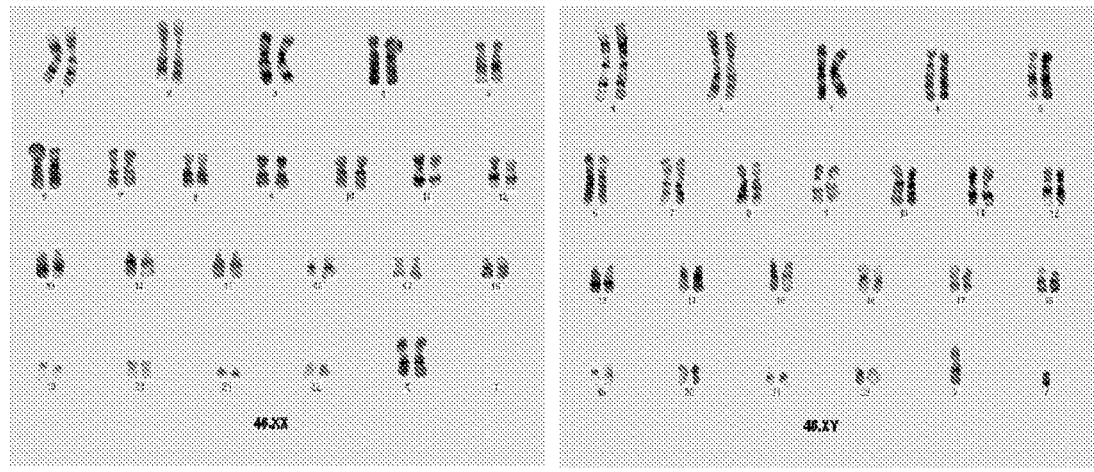

In another experiment, six mesenchymal stromal cell isolates were split and grown using media supplemented with either 10% FBS or 5% PL. After 12 passages, the cells were submitted for karyotype analysis. Two of the six cultures grown in FBS had abnormal karyotype, while none of those lines grown in PL were abnormal. The karyotypes from the two abnormal and their analagous lines grown in PL are shown in FIG. 35.

In addition to the initiation of primary tumor cultures derived from glioblastoma patients using PL, PL were used to initiate primary tumor cultures derived from surgical specimens obtained from patients with renal cell carcinoma.

Example 4—Analysis of Platelet Lysates

Figure 10:
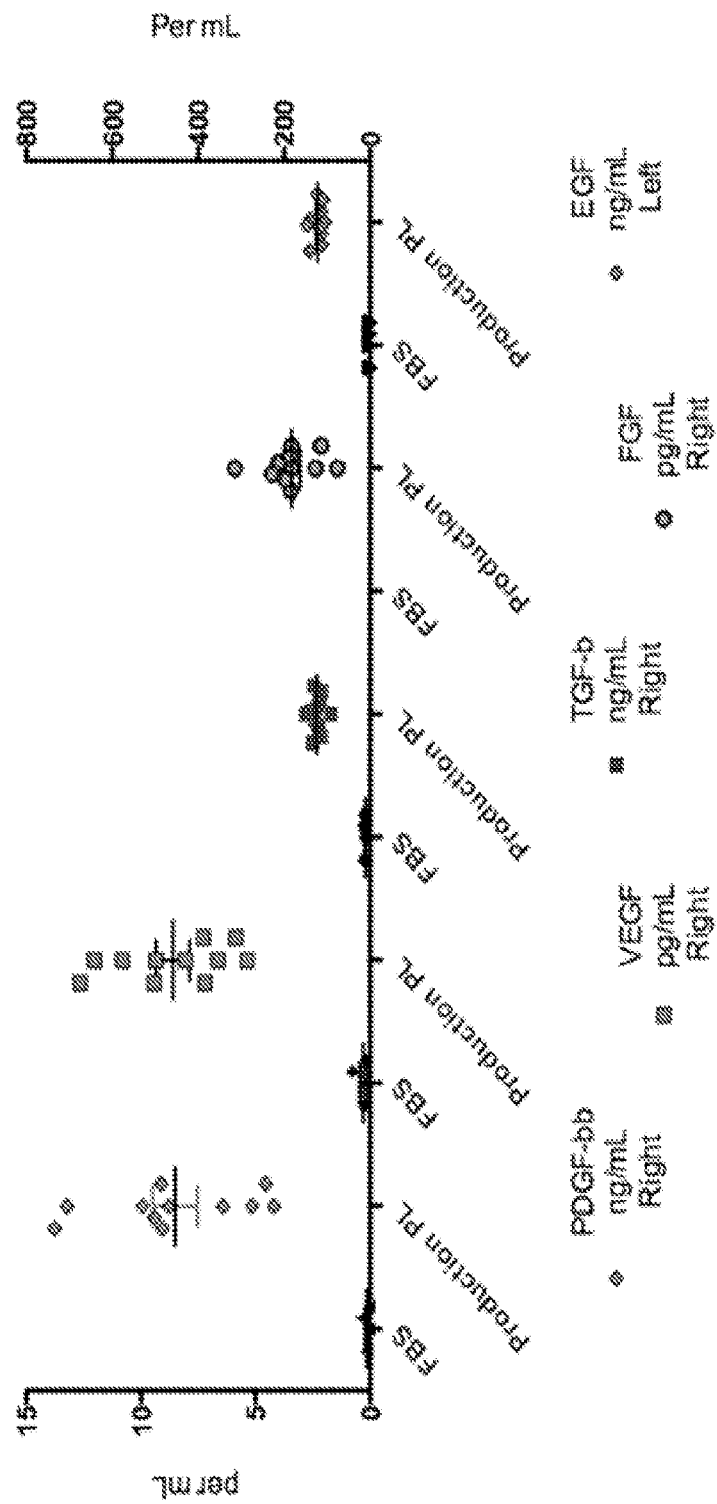
FIG. 10 is a graph plotting the typical amounts of the indicated growth factors found in manufactured platelet lysates. Eleven manufactured platelet lysate products (Production PL) were measured for the indicated growth factors by ELISA. The growth factor and the axis it uses are indicated below the columns. The amount of the indicated growth factors present within fetal bovine serum (FBS) was also measured.
Figure 11:
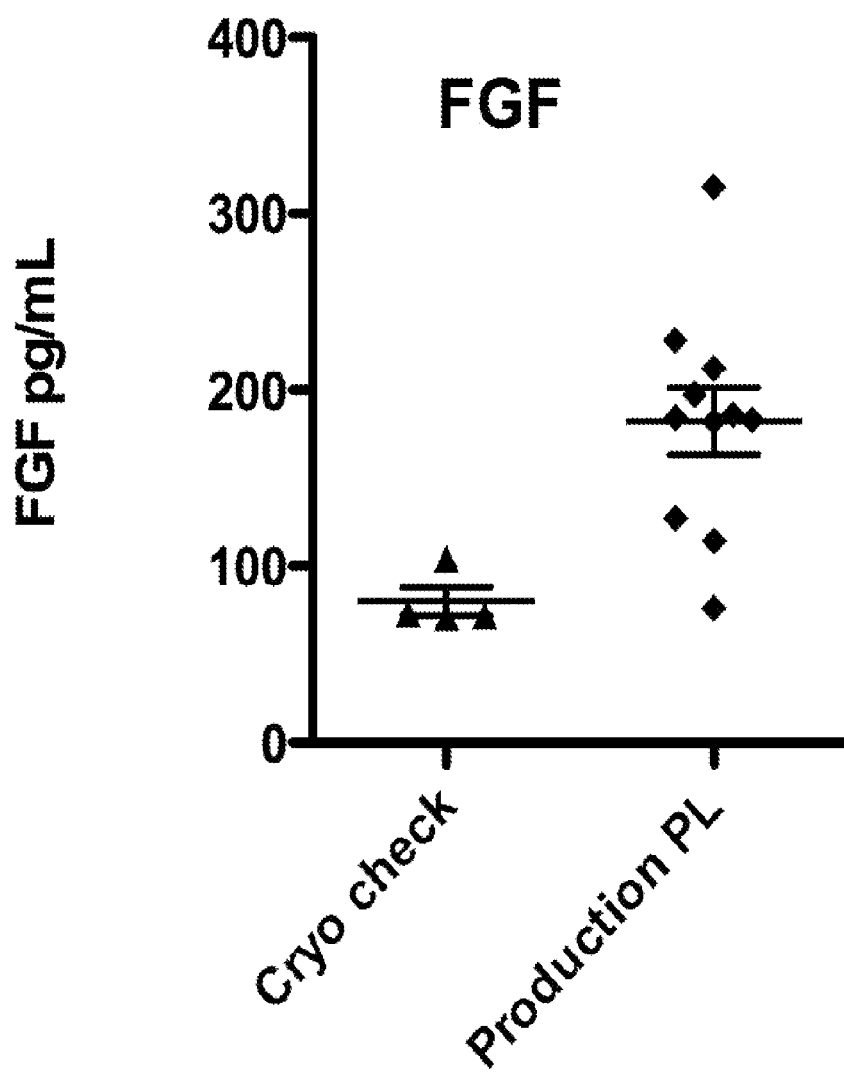
FIG. 11 is a graph plotting the amount of FGF (pg/mL) measured in platelet lysates produced as described herein (n=11) and in commercially available platelet lysates (Cryocheck; n=4).
Figure 12:
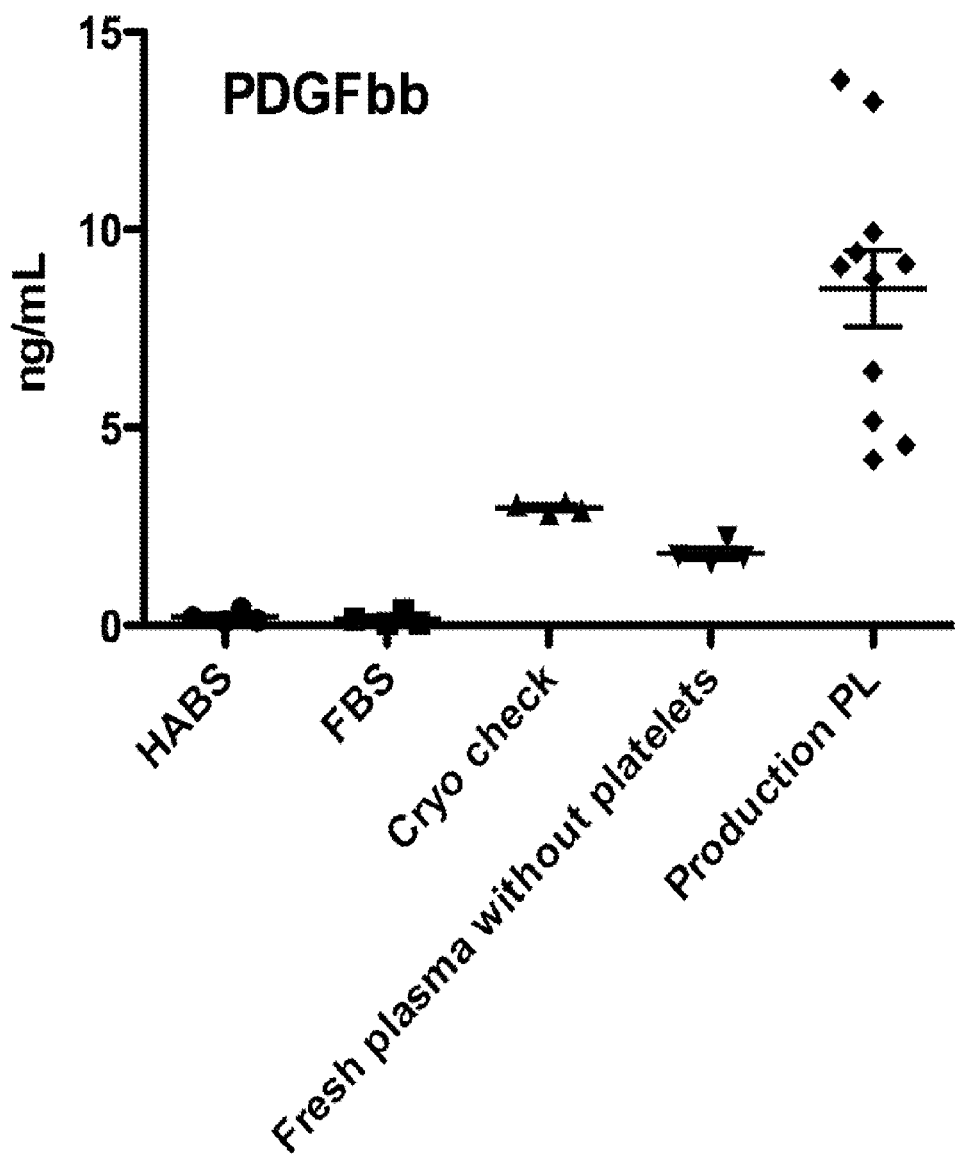
FIG. 12 is a graph plotting the amount of PDGF-BB (ng/mL) measured in platelet lysates produced as described herein (n=11), human AB serum (HABS; n=4), fetal bovine serum (FBS; n=4), commercially available platelet lysates (Cryocheck; n=4), and fresh plasma without platelets (n=4).
Figure 13:
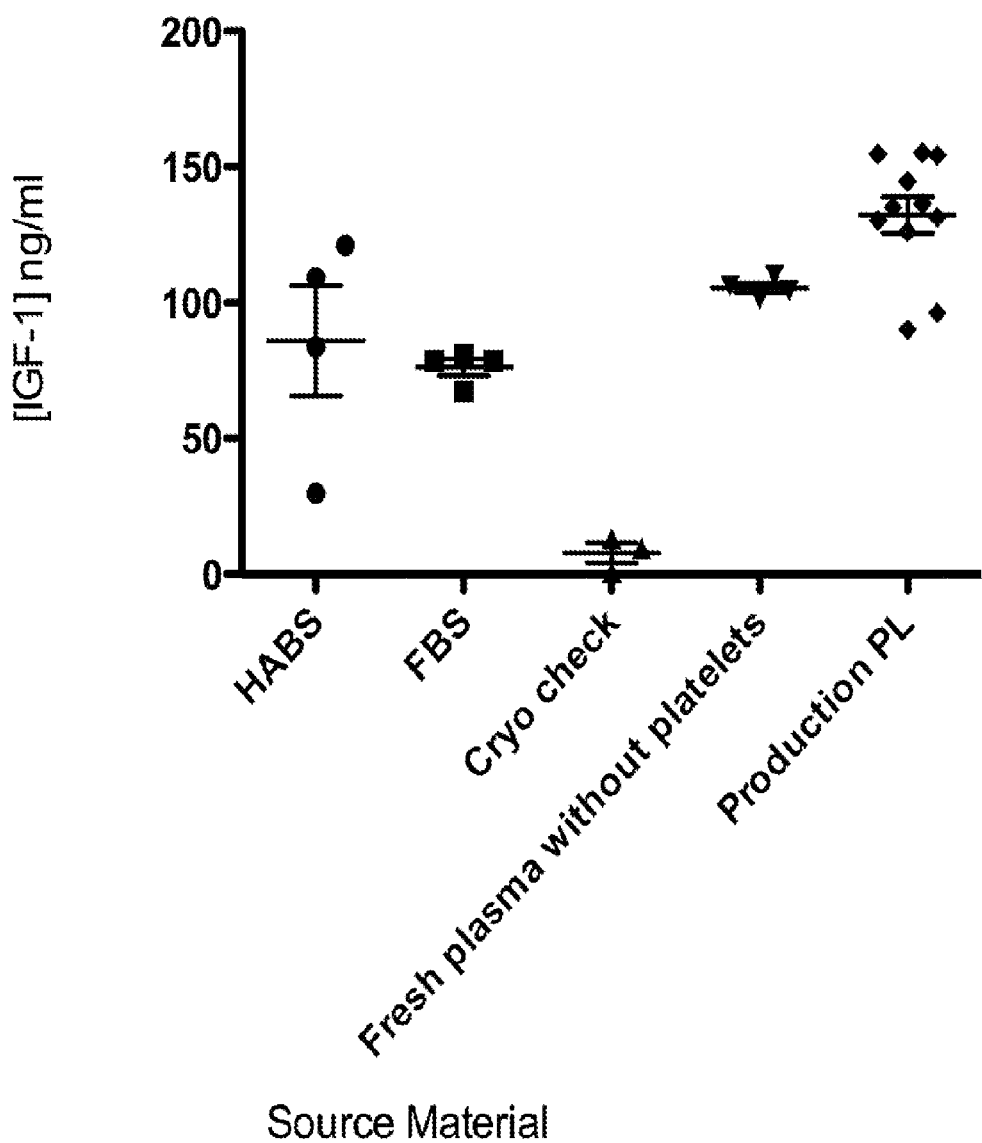
FIG. 13 is a graph plotting the amount of IGF-1 (ng/mL) measured in platelet lysates produced as described herein (n=11), human AB scrum (HABS; n=4), fetal bovine serum (FBS; n=4), commercially available platelet lysates (Cryocheck; n=3), and fresh plasma without platelets (n=4).
Figure 14:
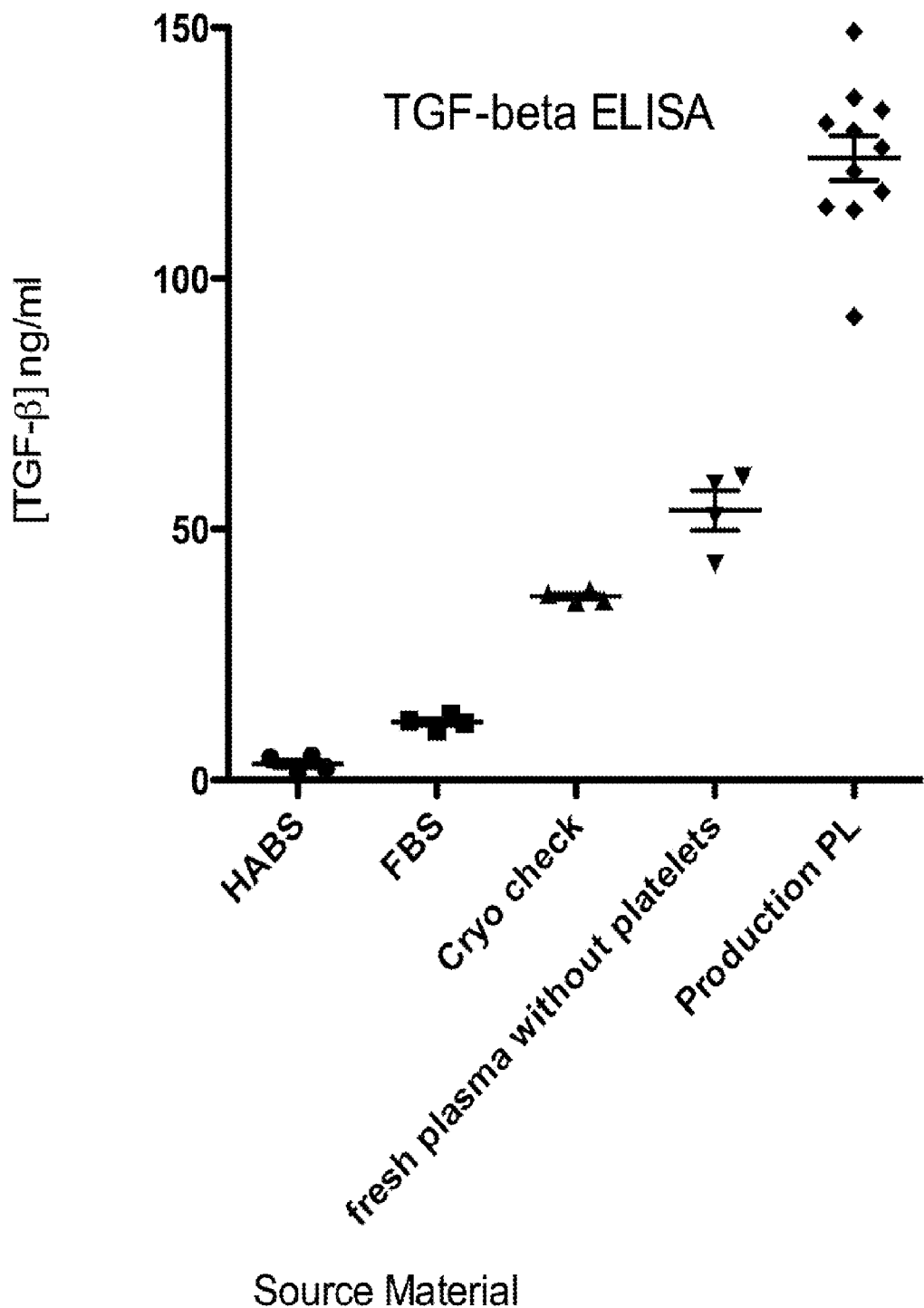
FIG. 14 is a graph plotting the amount of TGF-β (ng/mL) measured in platelet lysates produced as described herein (n=11), human AB scrum (HABS; n=4), fetal bovine serum (FBS; n=4), commercially available platelet lysates (Cryocheck; n=4), and fresh plasma without platelets (n=4).
Figure 20:
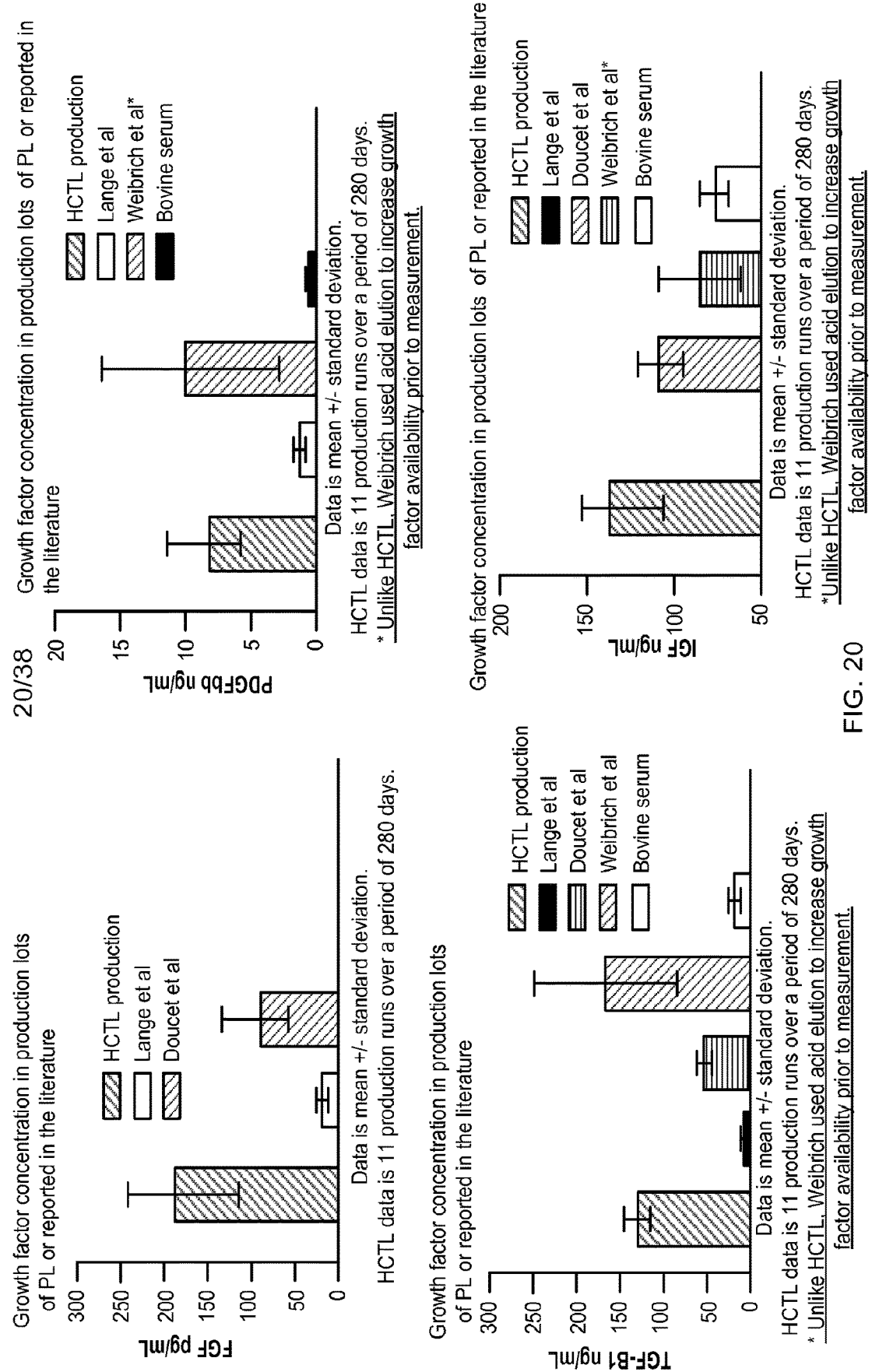
FIG. 20 contains four graphs comparing the levels of PDGF-BB, FGF, TGF-β1, and IGF-1 present with platelet lysates produced as described in Example 2 (HCTL production) to the levels of PDGF-BB, FGF, TGF-β1, and IGF-1 reported in the indicated references or bovine serum. Lange et al. is the Lange et al. reference (*Cellular Therapy and Transplantation*, 1(2) December (2008)); Weibrich et al. is the Weibrich et al. reference (*Craniomaxillofac. Surg.*, 30:97-102 (2002)); and Doucet et al. is the Doucet et al. reference (*J. Cell Physiology*, 205: 228-236 (2005)).

Eleven lots of platelet lysates manufactured as described in Example 2 (Production PL) were analyzed to determine the amount of EGF, FGF, IGF-1, PDGF-BB, TGF-$\beta$, and VEGF present as measured by ELISA. The measured amounts were compared to those measured in one or more of the following: fetal bovine serum (FBS), human AB serum (HABS), a commercially available platelet lysate (Cryocheck; catalog number PNP-10; Precision BioLogic, Inc., Nova Scotia, Canada) and fresh plasma without platelets. The typical amounts of EGF, FGF, PDGF-BB, TGF-$\beta$, and VEGF within the manufactured platelet lots as compared to FBS are presented in FIG. 10. The average amount of FGF within the manufactured platelet lots was about 180 pg/mL, while the average amount present within a commercially available platelet lysate was 80 pg/mL (FIG. 11). The average amount of PDGF-BB within the manufactured platelet lots was about 8.5 ng/mL, while the average amount present within a commercially available platelet lysate was 2.9 ng/mL (FIG. 12). The average amount of IGF-1 within the manufactured platelet lots was about 132 ng/mL, while the average amount present within a commercially available platelet lysate was 7.7 ng/mL (FIG. 13). The average amount of TGF-$\beta$ within the manufactured platelet lots was about 54 ng/mL, while the average amount present within a commercially available platelet lysate was 37 ng/mL (FIG. 14). The levels of PDGF-BB, FGF, TGF-$\beta$, and IGF-1 present in platelet lysates produced as described in Example 2 were compared to the levels of PDGF-BB, FGF, TGF-$\beta$, and IGF-1 reported in the literature or bovine serum (FIG. 20).

Figure 15:
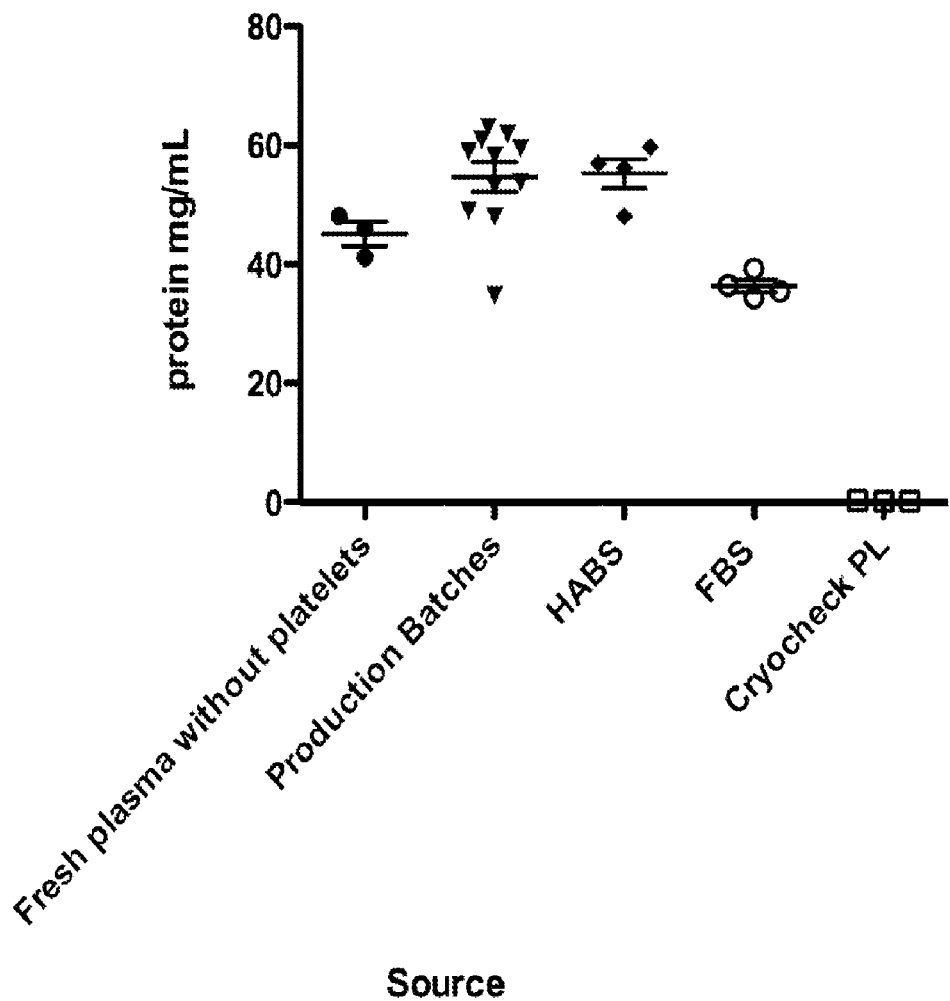
FIG. 15 is a graph plotting the amount of total protein (mg/mL) measured in platelet lysates produced as described herein (n=11), human AB serum (HABS; n=4), fetal bovine serum (FBS; n=4), commercially available platelet lysates (Cryocheck PL; n=3), and fresh plasma without platelets (n=3).
Figure 16:
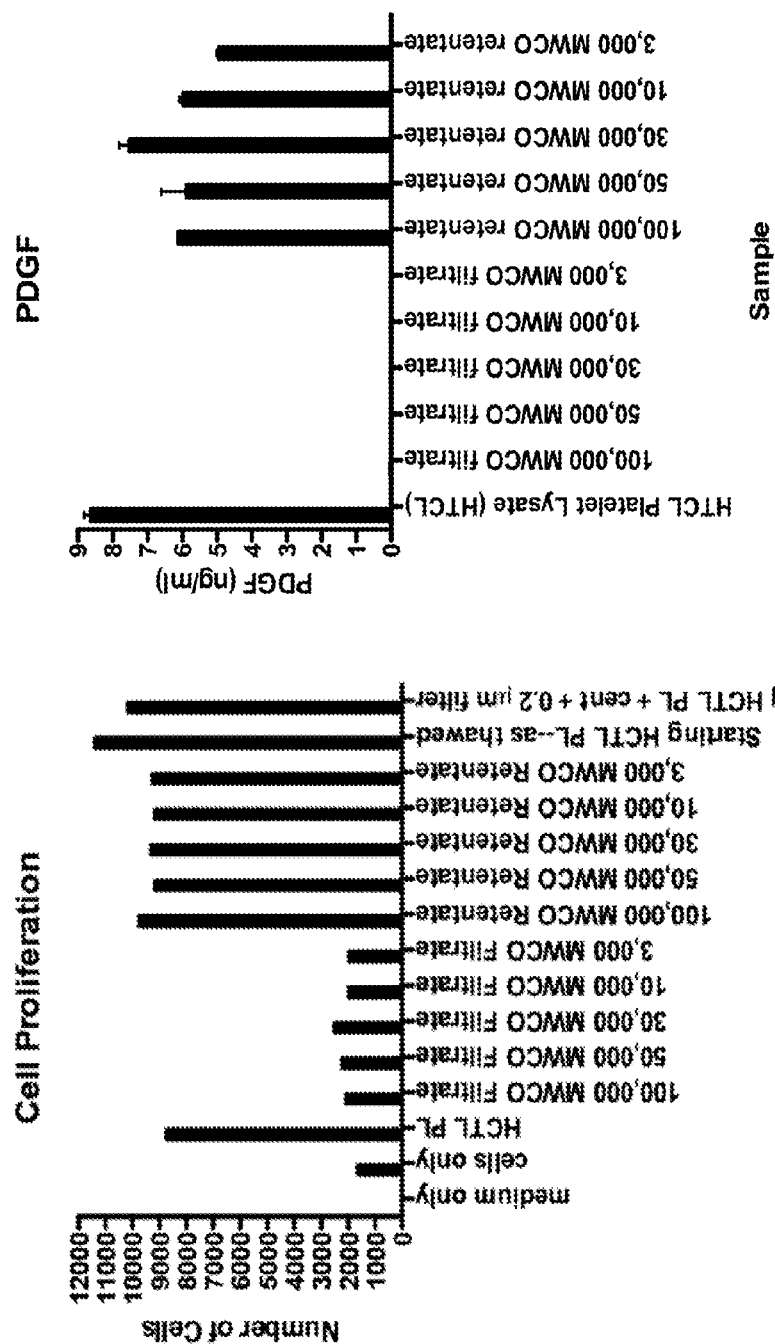
FIG. 16 contains a graph plotting the cell proliferation potential and presence of PDGF in PL fractionated using molecular weight cut-off filters. Cell proliferation calculated the number of cells after 800 cells/well were plated and grown for four days containing the indicated component and a graph plotting the amount of PDGF-BB (ng/mL) measured by ELISA in the indicated component. HCTL PL=5% PL using advanced MEM as the base media.

The total amount of protein within eleven lots of platelet lysates manufactured as described in Example 2 was measured using a modified Bradford assay. The average amount of total protein within the manufactured platelet lots was about 49 mg/mL, while the average amount present within the commercially available platelet lysates was 0.03 mg/mL (FIG. 15). The total amount of protein within the manufactured platelet lots was similar to the amounts measured in the fresh plasma without platelets, the fetal bovine serum, and the human AB serum (FIG. 15).

These results suggest that growth factor concentration alone is not responsible for the effective growth stimulating properties of the platelet lysates provided herein. The mean of the levels of growth factors present with the platelet lysates provided herein was about 2 to 3 times that of the commercially available platelet lysate. However, the commercially available platelet lysate was not different than fetal bovine serum. In addition, the platelet lysates provided herein had about 3000 times the amount of protein than that of the commercially available platelet lysates, yet protein alone cannot account for the activity as the platelet lysates provided herein since they exhibited similar levels of total protein as that found in human AB serum.

The following experiments were performed to assess the size of the material within the platelet lysate provided herein that contains PDGF-BB and the ability to stimulate cell proliferation. Briefly, platelet lysates were produced from an outdated platelet concentrate from a single donor. The number of platelets for each lysing condition was equal, and the volume used for lysing was equal for all modifications and equal to the volume of the platelet concentrate used for the unmodified condition. The platelet lysates were filtered on size selection filters with specific molecular weight cut-offs. The filtrate (less than the size indicated) and the retentate (greater than the size indicated) were analysed for the presence of PDGF-BB by ELISA and the ability to stimulate cell proliferation. To assess cell proliferation, 96-well tissue culture plates seeded with 800 adult adipose derived MSC cells were used with Advanced MEM (Gibco) media supplemented with 2 units/mL heparin and a preparation of platelet lysate (5%; v/v). PDGF-BB has a molecular weight of about 30 KDa (30,000 MW protein).

PDGF-BB was observed only in the retentates including the >100,000 preparations suggesting that all of the PDGF-BB is bound to complexes greater than this size. Also, proliferation occurred in cultures containing these larger (>100,000 Da) complexes. These results indicate that there are high molecular weight complexes containing growth factors that can be responsible for the activity of the platelet lysates provided herein.

Growth factors and other small proteins were found in large complexes in the platelet lysates provided herein. A platelet lysate (0.5 mL), which was thawed, centrifuged at 3,000×g, and filtered through a 0.2 mm filter, was applied to a 1.5 cm×27 cm column packed with Sephadex G-150-120 (Pharmacia Fine Chemical Company) and equilibrated with 50 mM sodium phosphate, 150 mM NaCl, pH 7.4 buffer. The chromatography was developed at a flow rate of 25 mL/hour, and the $A_{280}$ of each fraction was measured. Column fractions were analyzed by SDS-PAGE using a 4-15% Criterion gel (Bio-Rad Laboratories) and silver staining. This was a size exclusion analysis that resulted in the largest complexes being in the earliest fractions and the smaller complexes/single molecules being in the later fractions.

Figure 17:
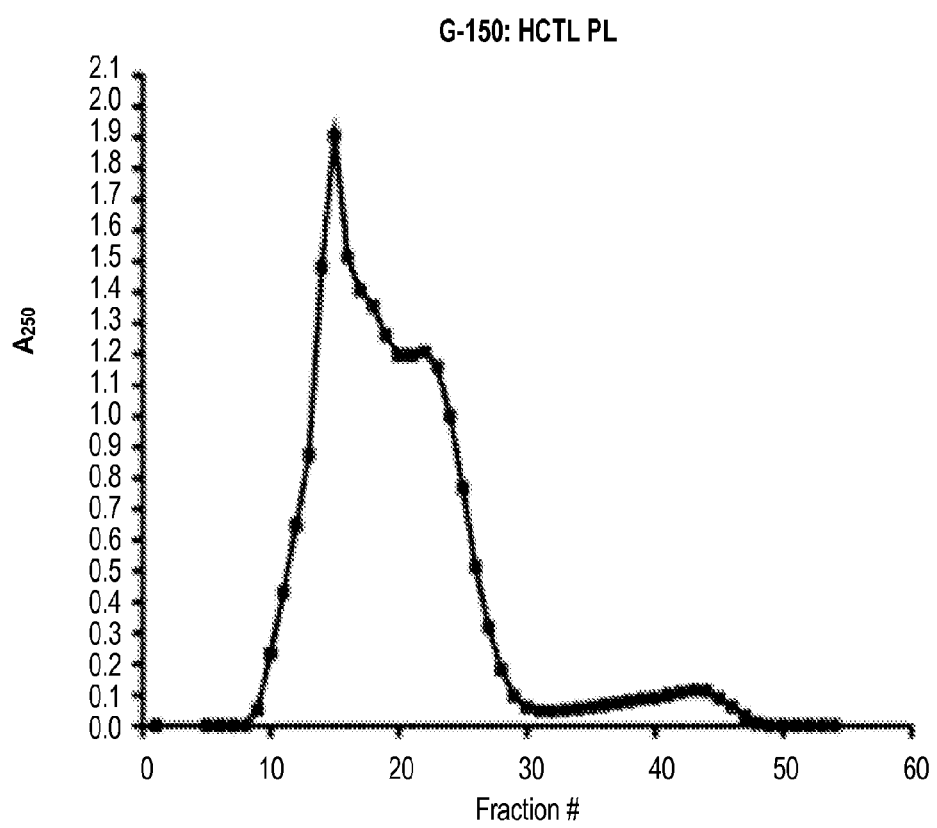
FIG. 17 contains a graph (top) plotting the $A_{280}$ for the indicated fractions of PL isolated by size fractionation and a photograph (bottom) of a silver stained reducing gel containing the indicated fractions.
Figure 17:
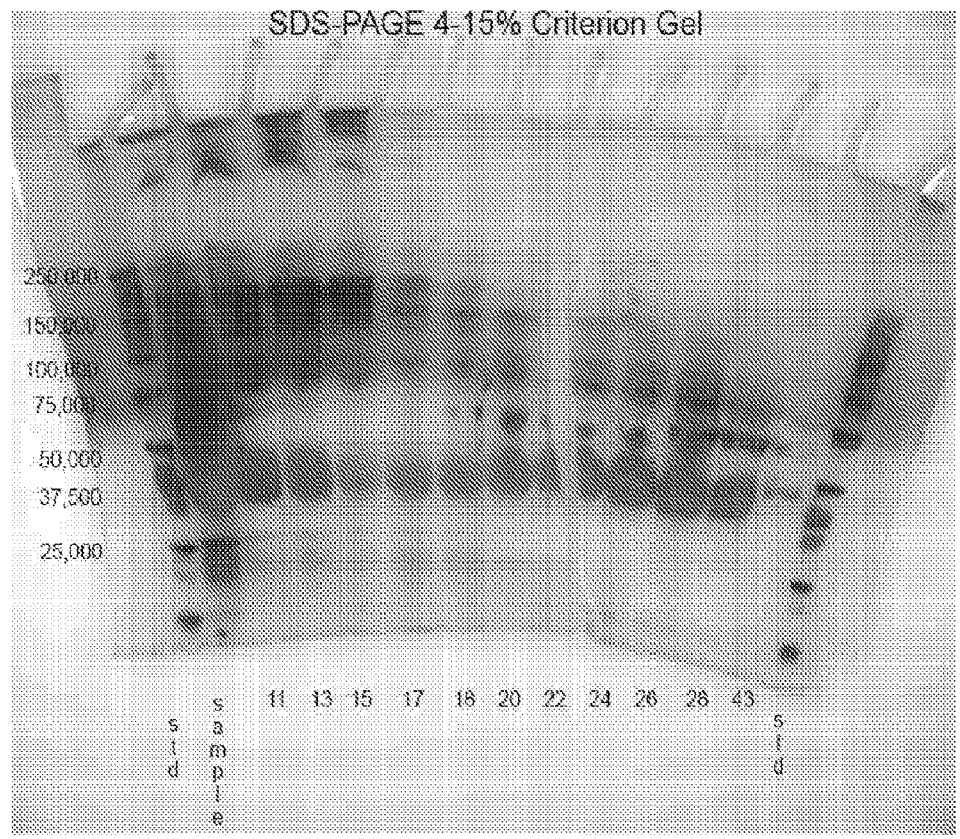

A large fraction of the platelet lysate flowed from the column right away (FIG. 17, top). To see the size of these complexes, these fractions were run on a reducing gel (FIG. 17, bottom). Early fractions contained proteins with a molecular weight less than 25,000 Da, suggesting that small proteins are bound to these large complexes.

Figure 18:
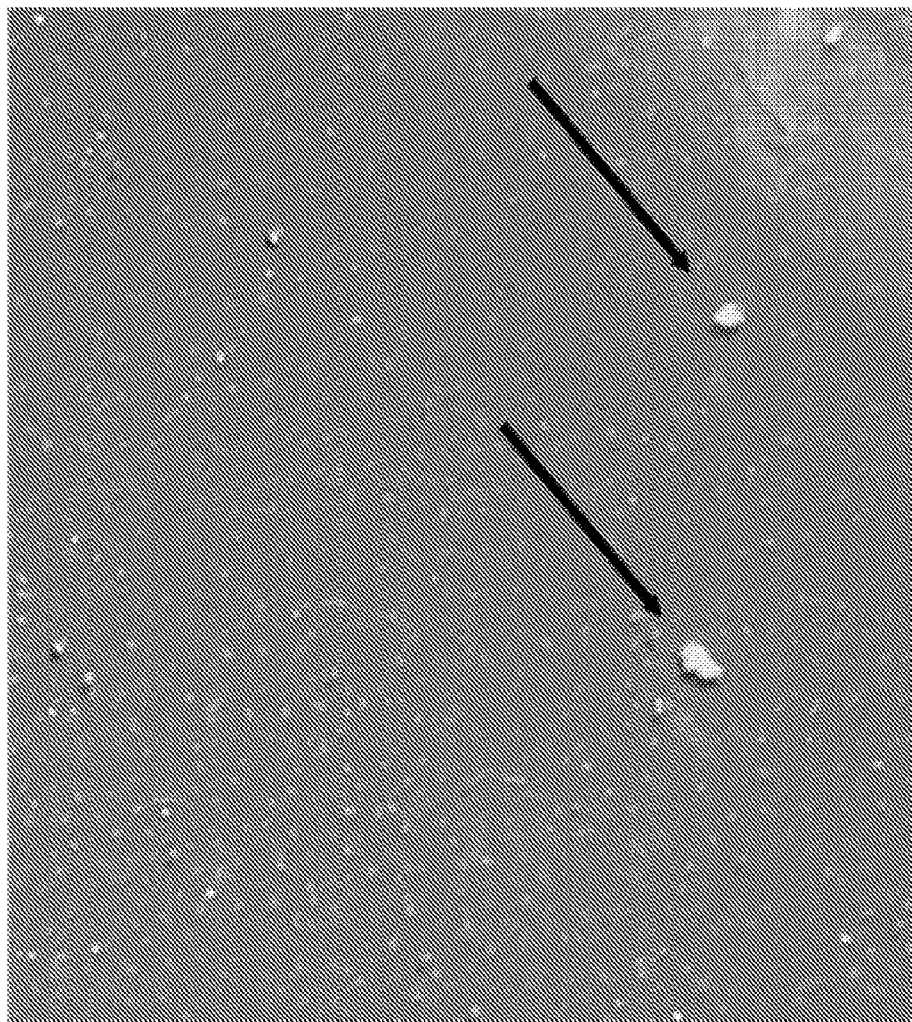
FIG. 18 is a scanning electron photograph of complexes present with a platelet lysate produced as described in Example 2.

A sample from platelet lysate manufactured as described in Example 2 was examined using a scanning electron microscope. As shown in FIG. 18, several large complexes are readily observable. Many particles were observed up to 0.2 μm in size.

Figure 19:
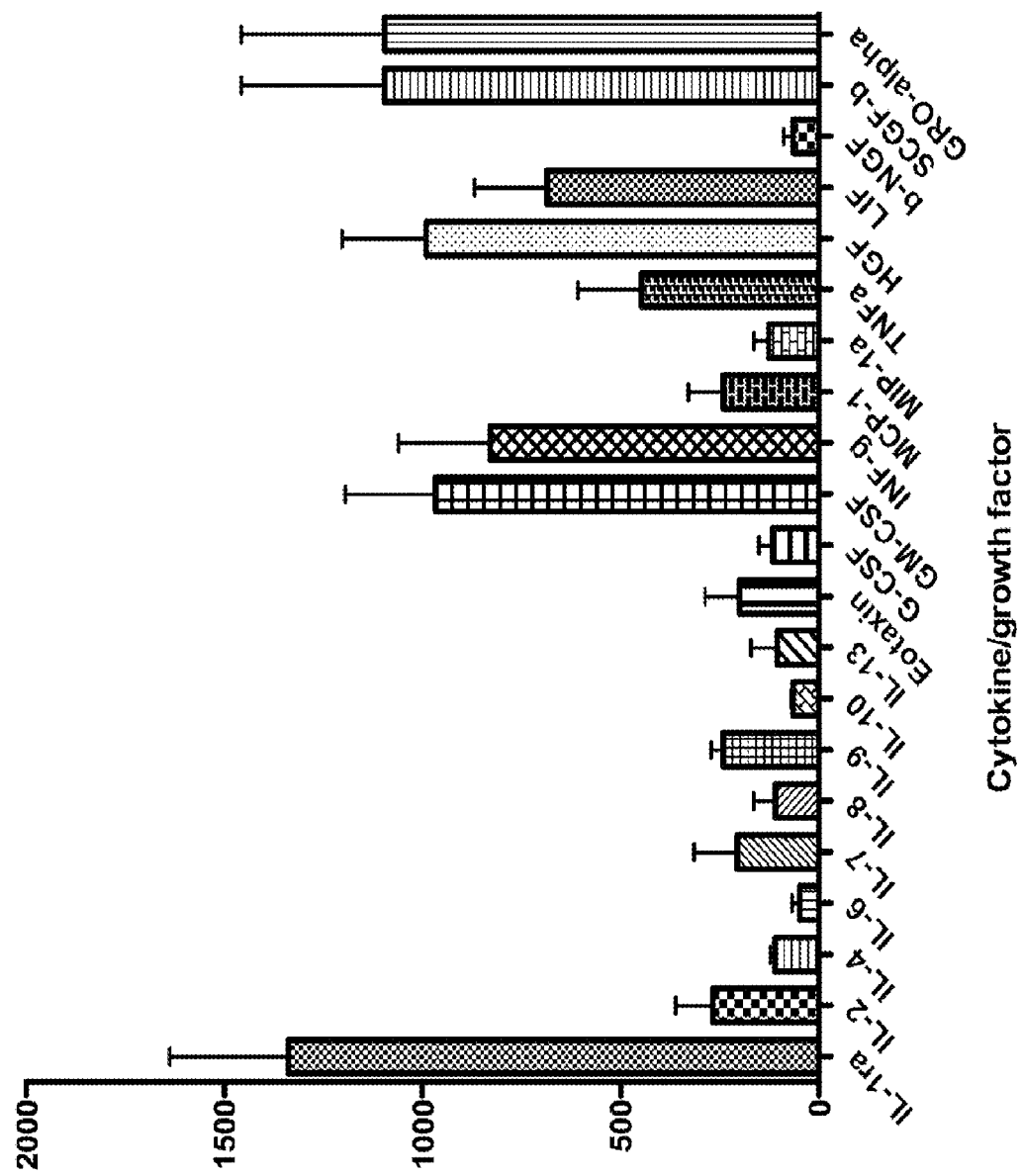
FIG. 19 is a graph plotting the amount of the indicated cytokine or growth factor present within platelet lysates.

In another experiment, 1-4 lots of platelet lysates manufactured as described in Example 2 were assessed to determine the amount of 21 cytokines and growth factors present within the platelet lysates using a BioPlex 26-plex assay (Biorad, Hercules, Calif.) per manufacturer's directions. The results are presented in FIG. 19.

Example 5—Culturing Cells Using Platelet Lysates

Figure 21:
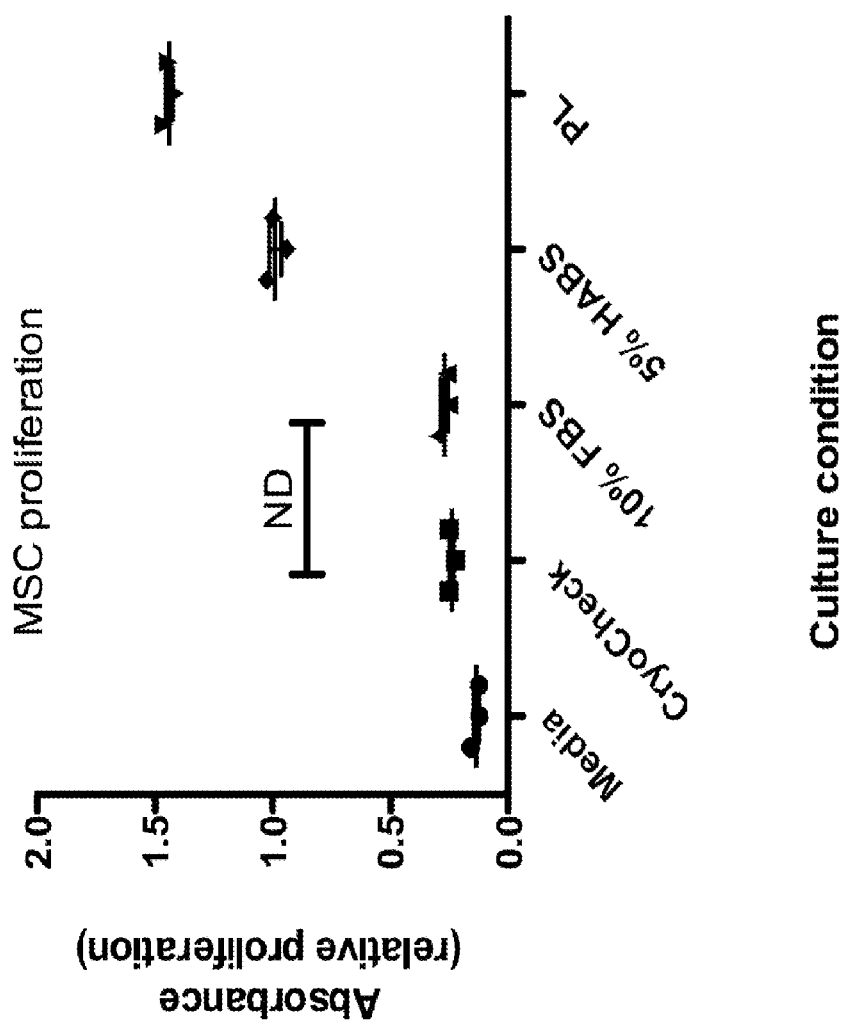
FIG. 21 is a graph plotting relative proliferation (absorbance) for MSCs cultured as indicated.

MSCs were thawed and grown in a-MEM with 5% PL until confluent. The cells were then passaged and split into a-MEM medium only or a-MEM medium with the following supplements: 5 percent (vol/vol) Cryocheck, 10 percent (vol/vol) FBS, 5 percent (vol/vol) HABS, or 5 percent (vol/vol) of a platelet lysate prepared as described in Example 2. Relative proliferation was assessed using absorbance measurements. The greatest amount of proliferation was observed with MSCs cultured in the presence of the platelet lysate prepared as described in Example 2 (FIG. 21).

Figure 22:
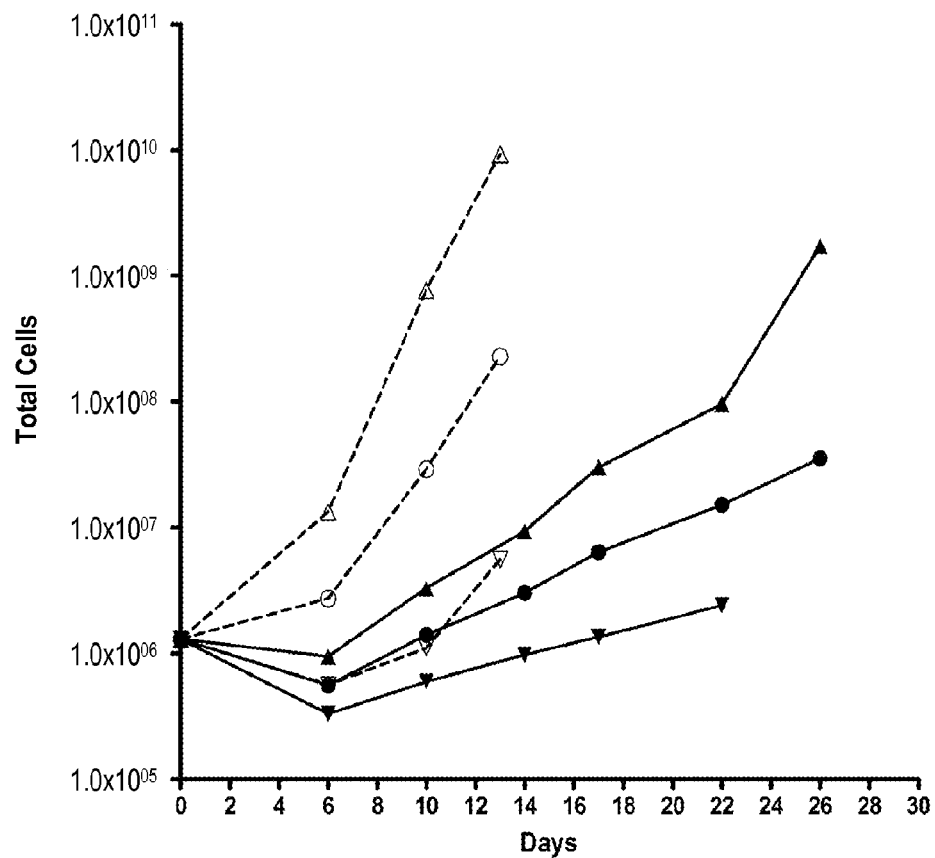
FIG. 22 is a graph plotting the cell count for adult stem cells cultured for the indicated number of days in medium (alpha-minimal essential medium (α-MEM)) supplemented with 5 percent of a platelet lysate produced as described in Example 2 or medium supplemented with 10 percent fetal calf serum.
Figure 23:
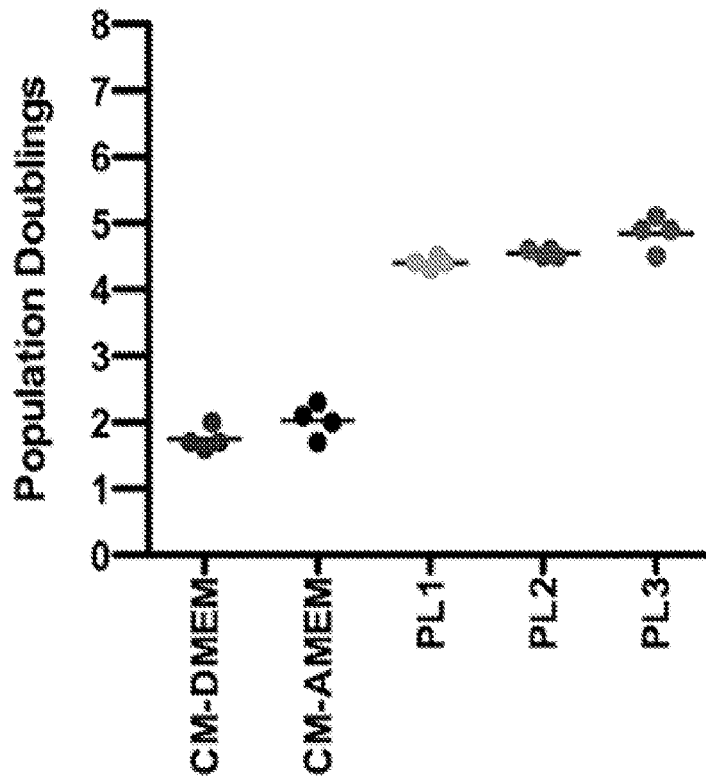
FIG. 23 is a graph plotting the population doublings for MSCs cultured in the indicated media.

In other experiments, adipose tissue MSCs were observed to grow faster in the presence of 5 percent of a platelet lysate produced as described in Example 2 than in 10 percent fetal calf serum (FIGS. 22 and 23).

To determine the immune modulating effect of PL, PL was used as a supplement instead of human AB serum in culture conducive to the differentiation of CD14+ monocytes into the immune stimulating cells dendritic cells (described in Dietz et al., *Transfusion*, 46(12):2083-9 (2006)). PL were incubated for the entire culture condition or for the last stage (day 3-6) of dendritic cell culture characteristic of generating active mature dendritic. The changes associated in the culture were measured with particular emphasis on the expression of CD80 and CD83; two characteristic markers of dendritic cell culture. No effect of the PL as a supplement was observed in these conditions. Thus, PL appears to have a benign effect on the immune response.

Figure 27:
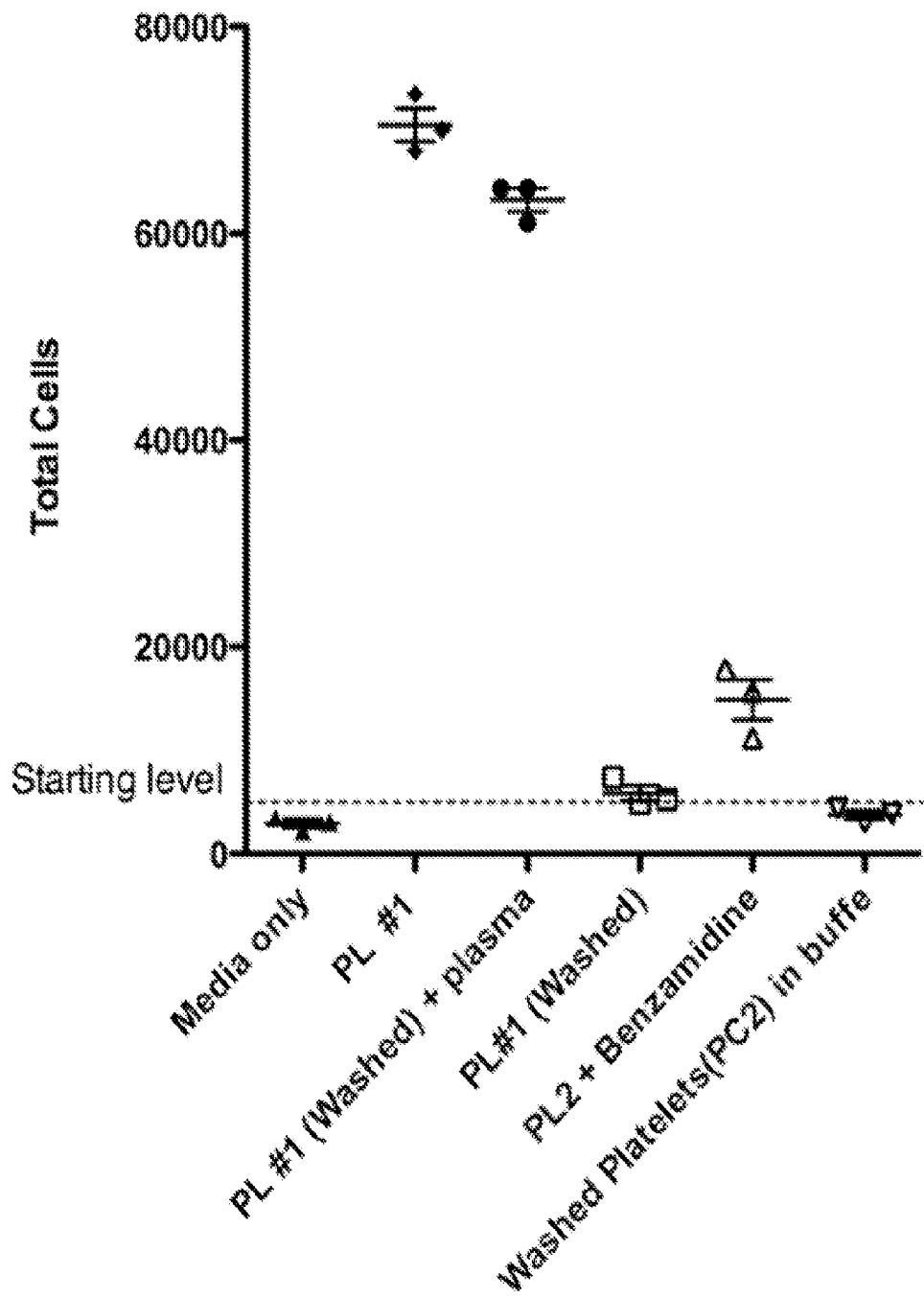
FIG. 27 is a graph plotting the total MSCs after five days of culture with the indicated compositions.

In another experiment, MSCs were plated in media, and cell growth was determined by counting. The media supplements were as follows: (a) none (media only), (b) PL #1 (platelet lysate manufactured in the presence of plasma), (c) washed PL #1+plasma (platelet lysate manufactured after removal of plasma followed by adding back plasma), (d) PL #1 washed (platelet lysate manufactured after removal of plasma), (e) PL2+Benzamidine (platelet lysate manufactured in the presence of plasma plus the clotting inhibitor benzamidine), and (f) washed platelets (PC2) in buffer (platelets manufactured in the absence of plasma). Cell proliferation was observed in cells cultured with PL #1 and cells cultured with washed PL #1+plasma (FIG. 27). Little or no proliferation was observed with cells cultured under the other conditions (FIG. 27). These results suggest that both plasma and clotting factors can be required to produce an effective composition containing platelet contents.

Example 6—High Efficiency Establishment of Primary Glioblastoma Cultures for Drug Discovery, Drug Optimization, and Anti-Tumor Vaccines Patient-derived primary glioblastoma multiforme (GBM) cell cultures applicable for clinical translation are produced. The culture medium described herein containing platelet contents is used for a highly efficient establishment of tumor cell cultures. The medium is likely more relevant to tumor growth than other methods and can be optimized for clinical-scale production compliant with Good Manufacturing Practice (GMP) requirements.

The effect of media supplementation with platelet contents on tumor culture was tested by splitting primary tumors and incubating them in one of three culture methods. The first culture included 10% fetal calf scrum (FCS or FBS) in culture media. The second culture contained culture media used to culture tumor stem cells (Neural stem cell media, NSC; Piccirillo and Vescovi, *Expert Opinion on Biological Therapy*, 7(8):1129 (2007); Fan et al., *Seminars in Cancer Biology*, 17(3):214 (2007)). The third culture media contained media supplemented with 5% human platelet derived media supplement (platelet lysate, PL).

Figure 28:
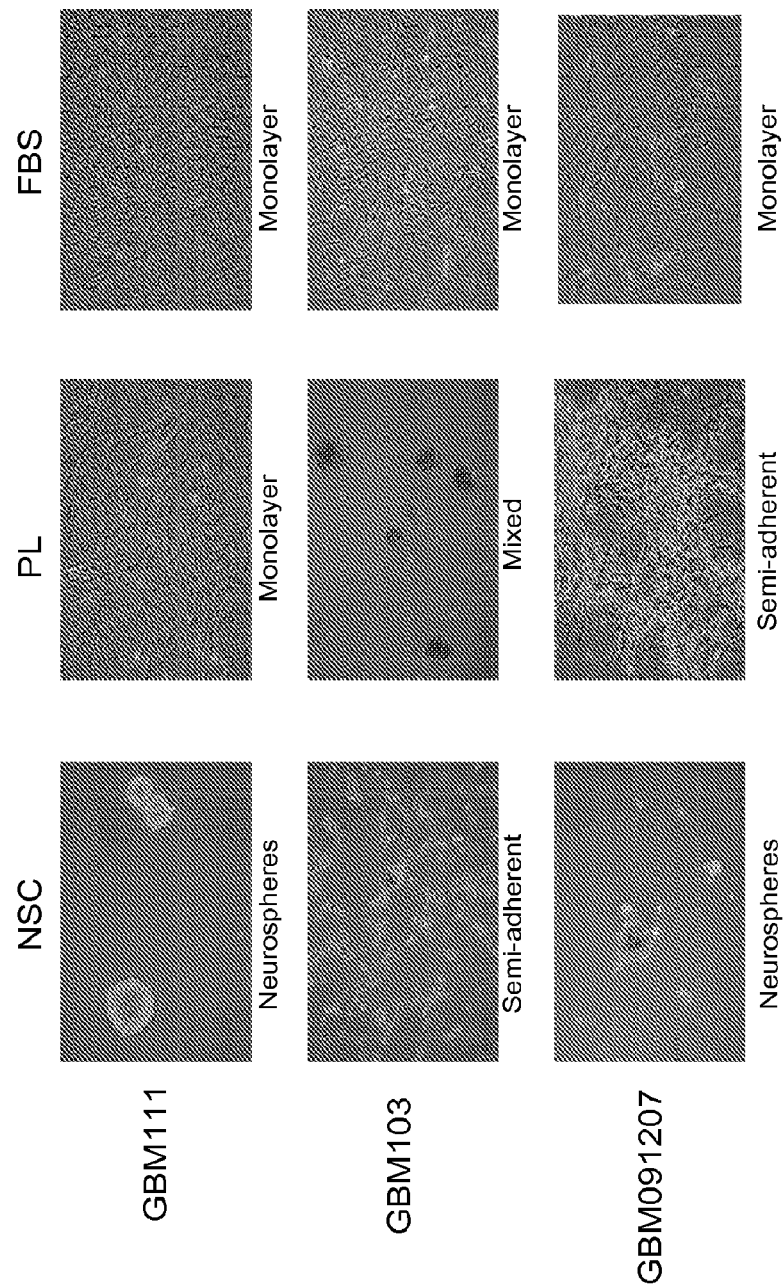
FIG. 28. Effect of culture condition on cell adherence. Tumors (in rows) were physically and enzymatically digested and incubated in three culture conditions (NSC, neural stem cell; PL, platelet lysate; or FBS, fetal bovine serum). Cells were photographed and descriptions of the morphology listed.

The effect of media supplementation was clear (FIG. 28). In response to the culture conditions, cells self-adhered forming spheres, preferentially adhered to the plastic forming monolayers, or cultures with mixed adherence. FBS cultures were uniformly adherent monolayers, with NSC media mostly having spheres or non-adherent cells. PL cultures existed within the complete spectrum of cell morphology. Cells continued in culture and were counted at each passage. PL was superior to other methods in the ability to generated large numbers of cells (FIG. 29). Importantly, cells grown in PL demonstrated a constant growth rate for more than 10 doublings in the absence of an initial lag phase, suggesting an immediate proliferation response upon plating (FIG. 29, left panel). Therefore, PL induced immediate and profound proliferation in many primary tumor cultures. Of the sixteen tumors cultured thus far, a 56% success rate of establishing primary cell growth was obtained, and a 44% rate of generating greater than 30 million cells in 60 days was obtained. Not a single culture grown in FBS could meet the latter requirement. Thirteen percent of the tumors grown in NSC conditions met these criteria. Interestingly, there was one cell culture that grew equally well in PL and NSC, and only one cell culture that grew uniquely in NSC. Overall, PL were greater than 3 times better at establishing primary tumor cultures than the next best method.

A criticism of FBS established cell cultures is that they are considered to have lost the undifferentiated nature of the in vivo tumor. To determine if cells cultured in PL have characteristics of tumor stem cells, the expression of nestin, Sox2, and CD133 was measured in PL cultured cells. The majority of cells in all cultures were nestin and Sox2 positive. Four of the seven cultures tested for CD133 expression had levels above background with one culture having more than 30% of the cells positive for CD133. These results suggest that indeed the cultures contain cells that have characteristics of tumor stem cells.

To determine the genetic stability of cultures grown in PL, human adipose derived mesenchymal stem cells from non-malignant donors were incubated in PL supplemented media. No abnormal karyotypes were found in up to twelve passages of cells. Thus, PL maintained the genetic integrity of normal cells in culture. GBM cultures were karyotyped and found to maintain a stable karyotype despite massive cell doublings (see, e.g., GBM106; FIG. 24C). In some cases, cultures consisted of stable subclones. The tumor cultures exhibited characteristic deletions (such as pten) and expressed tumor antigens such as EGFr, survivin, and IL13-r. Taken together, these results suggest that PL is a highly effective growth supplement for the establishment and proliferation primary tumor cultures.

An additional benefit of PL as a growth supplement is its source. Out-dated human platelets, approved-for-human-use, were used. This material was approved for therapeutic use with all the commensurate testing completed.

Thus, the methods and materials provided herein can allow to the generation of autologous tumor cells for use in patient specific vaccines, or other immune modulatory protocols where patient specific material may be required. The efficient in vitro generation of tens of millions of cells from >40% of all GBM tumors can allow for many new approaches to cancer treatment, including (a) the possibility to generate sufficient patient specific materials for repeated vaccinations for immune therapy protocols, (b) the establishment of a primary tumor cell library for drug screening on cell cultures having substantially fewer passages and more relevant material, (c) the development of specific drug screening protocols for patient specific optimization of chemotherapy, and (d) the cataloguing of the molecular profile of these primary tumor cultures and the association of these profiles with chemo-sensitivity.

A clinical trial is performed to confirm the use of autologous primary GBM cell cultures, which are produced as described herein, as an antigen source for vaccine studies. Primary cell cultures are established from material obtained at surgery. Patients undergo standard care.

The patient begins vaccinations using the primary cell cultures combined with immune stimulating adjuvants. Possible adjuvants for a tumor vaccine include dendritic cells, alum, GM-CSF, LPS, KLH etc. as well as other promising adjuvants.

In some cases, the generated cGMP material is used directly as tumor antigen for allogeneic donors. Patients have their tumors molecularly matched to the corresponding library, a match is identified, and is subsequently used for treatment.

To identify additional cancer treatments, the cell cultures produced as described herein are screened for drug-mediated suppression of cell growth using compounds from the NIH clinical collection. This collection represents drugs used in early phase clinical trials with described adequate safety profiles and commercial availability. Drugs identified as candidates for cell suppression are tested in vivo on the same tumors growing in immune deficient mouse models. Likewise, drugs identified as candidates are matched to the transcription profile or if the patient cells are growing fast enough, drugs tested on the patient material and used on the patient allowing patient specific drug screening and use.

Example 7—Stability of Platelet Lysates

Platelet Lysate

Platelet lysate was manufactured as described in Example 2. Immediately after manufacture, PL was aliquotted into multiple vials and transferred to −70° C., 5° C., 25° C., or 37° C. for long-term storage. Sufficient aliquots were transferred such that samples were maintained at a single temperature until analysis. Thus, the data represent samples stored at a constant temperature for the time indicated. Three independent lots of PL were analyzed for the presence of growth factors and two for the ability to proliferate MSC.

Analysis Methods

MSC Proliferation: Adipose derived, adult mesenchymal stromal cells (MSC) were obtained from fat collected as waste from gastric by-pass surgery. Fat was processed, and MSC were expanded and frozen until use in these assays. For these assays, MSC were thawed and allowed a single passage prior to plating for analysis. Growth was determined using the BioVision Quick Cell Proliferation Assay Kit II (Mountain View, Calif.). This assay is based on the cleavage of tetrazolium salt to formazin by cellular mitochondrial dehydrogenase. The amount of dye cleaved is proportional to live cells. Briefly, MSC were plated at $1 \times 10^4$ cells per well in RPMI1640 containing the designated amount of PL from the indicated conditions. The cells were incubated for 48 hours in 37° C., 5% $CO_2$ humidified incubator. The detection reagent was added (10 mL of WST) to each well. The plate was incubated for one hour, and the O.D. measured per manufacturer's directions.

Growth Factors: An ELISA test on PL that was stored at the indicated temperatures was used to determine the concentration of the growth factors of interest. All ELISAs were from R&D Systems (Minneapolis, Minn.) and used according to manufacturer's instructions.

Results

Growth of MSC in PL followed a typical dose response curve. Seventy percent of the capacity of MSC growth was observed using 20% of the typical amount of PL as a supplement. Thus, 1% PL media supplementation resulted in approximately 70% of the growth capacity.

Figure 30:
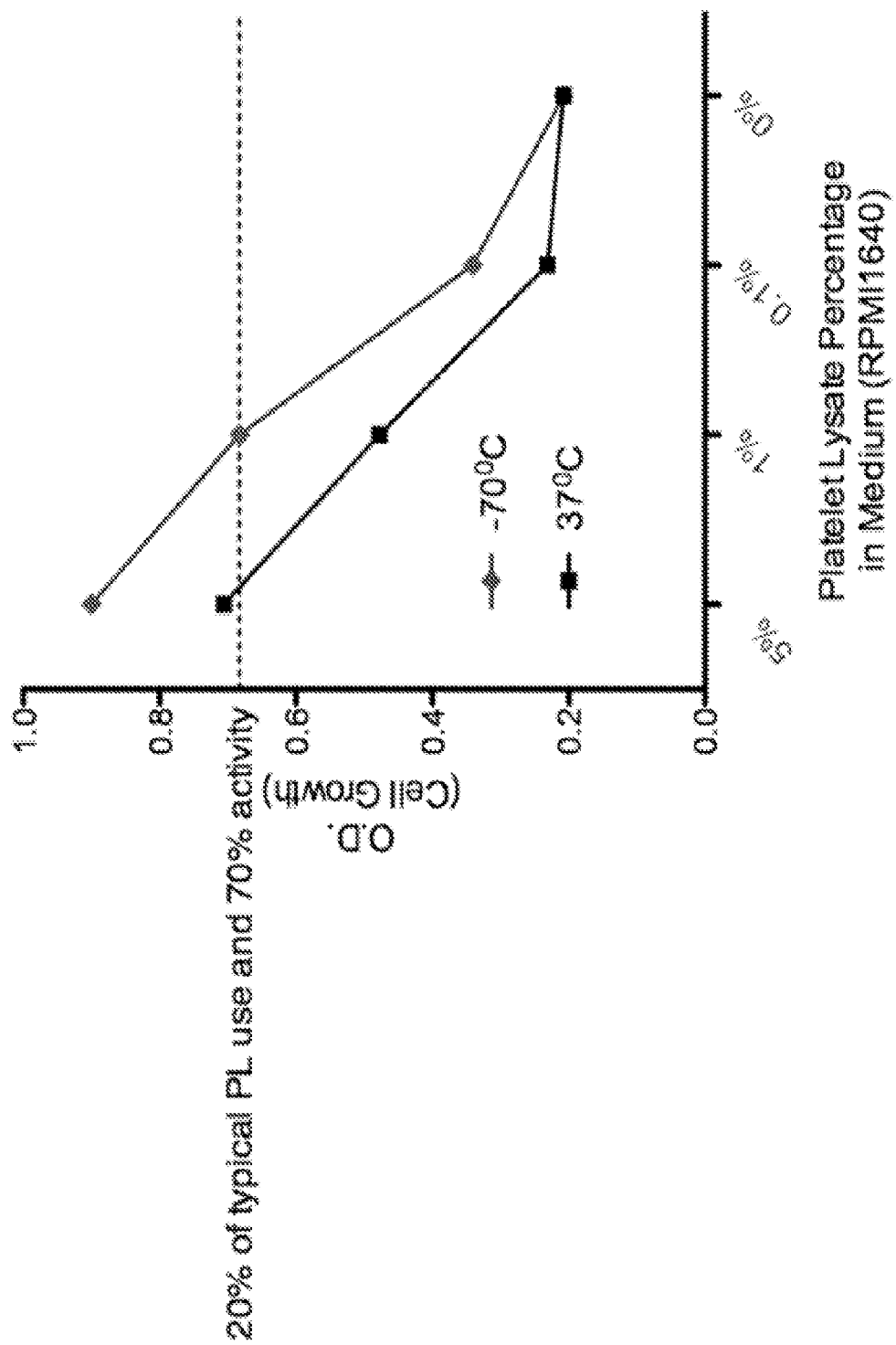
FIG. 30 is a graph plotting cell growth observed with the indicated amount of platelet lysate (PL).

Long-term storage of PL at 37° C. reduced, but did not eliminate, MSC growth (FIG. 30). MSC were cultured with different concentrations of PL that had been maintained at −70° C. or 37° C. for 48 days. There was a typical dose response curve observed for both PL incubated at −70° C. and 37° C. Interestingly, the PL incubated for this long at body temperature maintained its ability to stimulate 70% of the expected growth of PL at a similar concentration.

Figure 31:
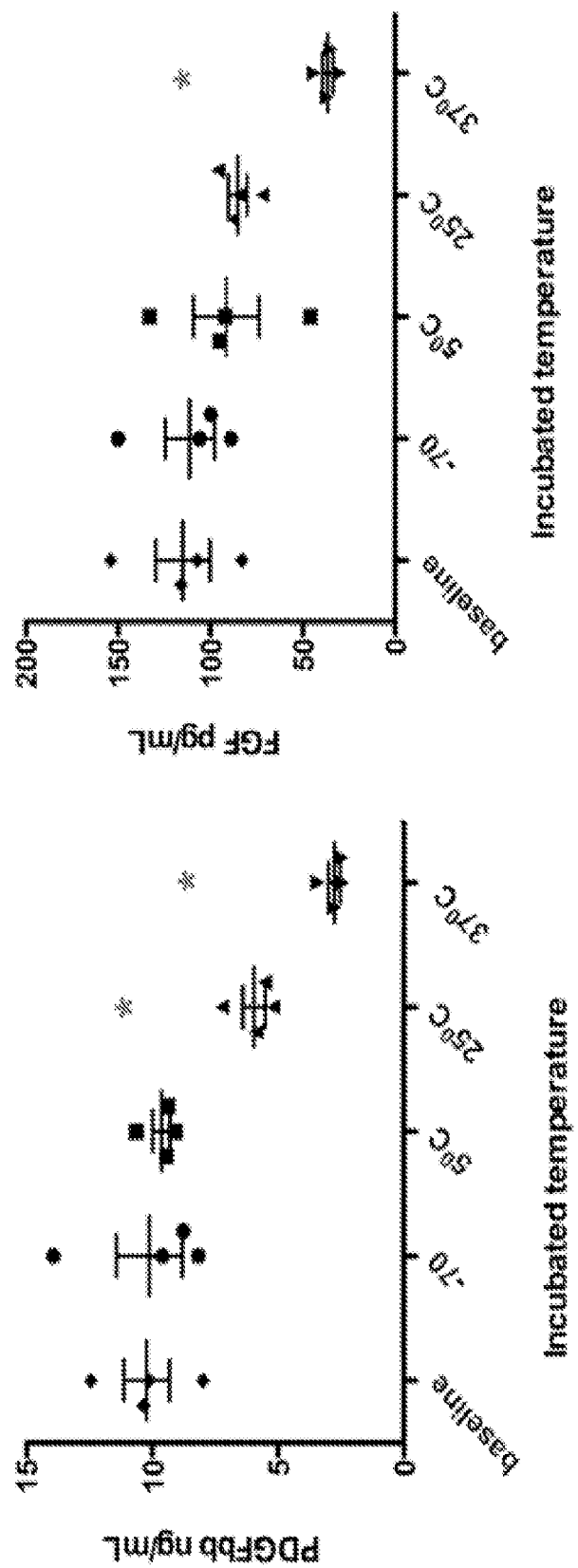
FIG. 31. Presence of PDGF and FGF in PL after 48 days of incubation at different temperatures. PL samples were incubated at the temperatures identified for four different lots of PL. Growth factors were measured by ELISA. Each dot represents the mean of three samples from that lot incubated at that temperature. Data plotted is the means from each of these lots. Bars are the mean of four lots, with changes represented by asterisk (p<0.05 for paired samples).
Figure 32:
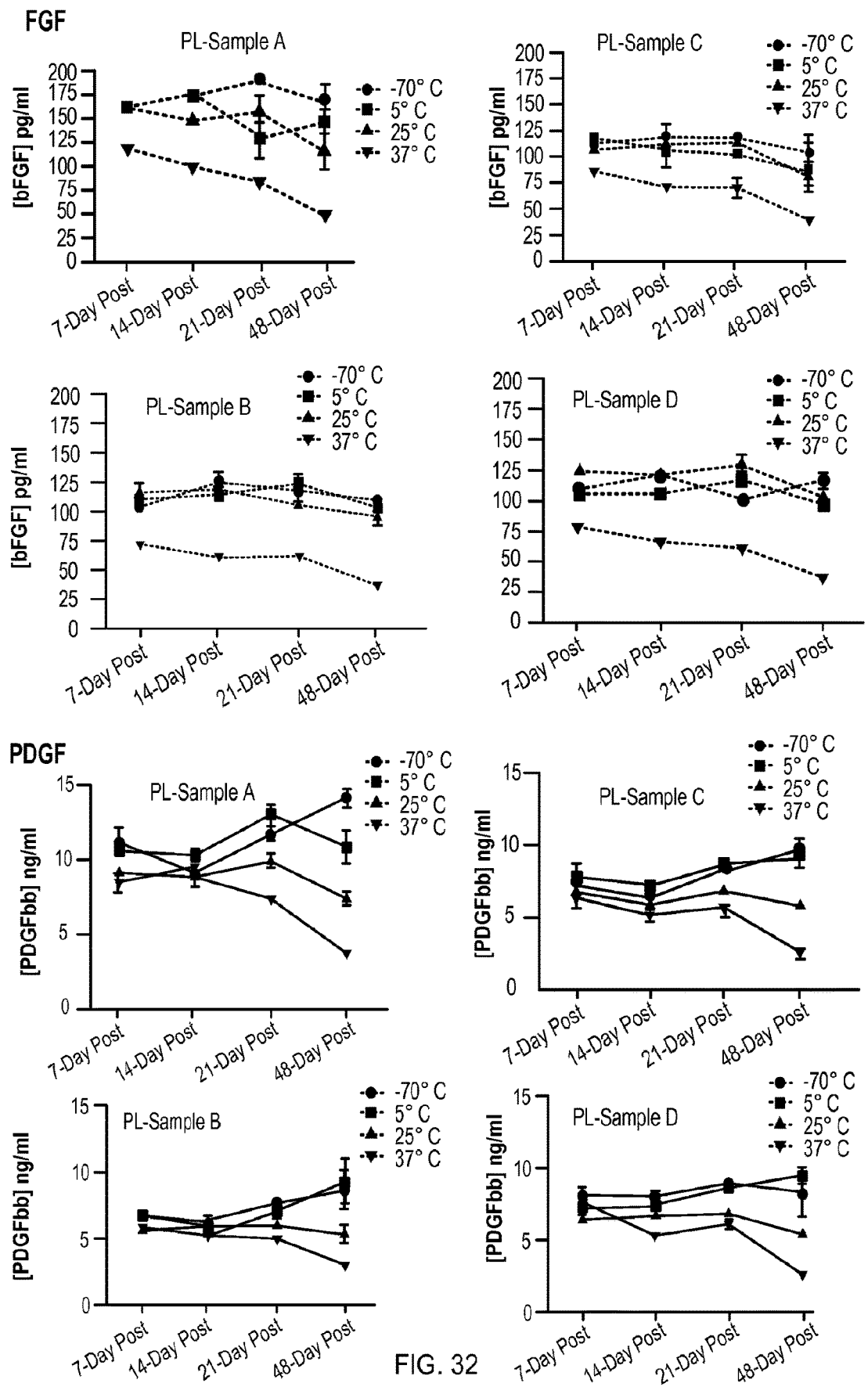
FIG. 32 is a graph plotting the amount of PDFG and FGF in PL samples incubated at the indicated temperatures.

To identify possible changes in growth factor concentrations associated with the reduction in growth of MSC, the levels of FGF and PDGF were measured in four lots of PL held at −70° C., 5° C., 25° C., and 37° C. (FIGS. 31 and 32). These concentrations were measured immediately after production, and on days 7, 14, 21, and 48.

When PL was stored at 37° C. for 48 days, FGF levels fell to 36.5±5.8 pg/mL compared to baseline levels of 115±29.5 and to 111.3±26.8 when PL was stored for 48 days at −70° C. This reduction was significant ($p<0.01$ and a reduction of approximately 32%; data represents mean from N=4 PL lots where each lot was measured using three independently stored samples). No reduction in concentrations of FGF was observed when it was stored for this amount of time at 5° C. or 25° C.

Similarly, when PL was stored at 37° C. for 48 days, PDGF levels fell to 2.8±0.4 ng/mL compared to baseline levels of 10.2±1.8 or 10.1±2.6 when PL was stored for the same amount of time at −70° C. This reduction was significant ($p<0.01$ and a reduction of approximately 27%). Additionally, a temperature dependent reduction in the amount of PDGF measured when the PL was stored at 25° C. (mean=6.0±0.9 and p=0.02) was observed. Thus, the loss in the growth factors approximates the loss in the MSC growth stimulating capacity. To calculate the shelf life, the changes in growth factors over time and temperature were used.

Estimation of Shelf Life

Figure 33:
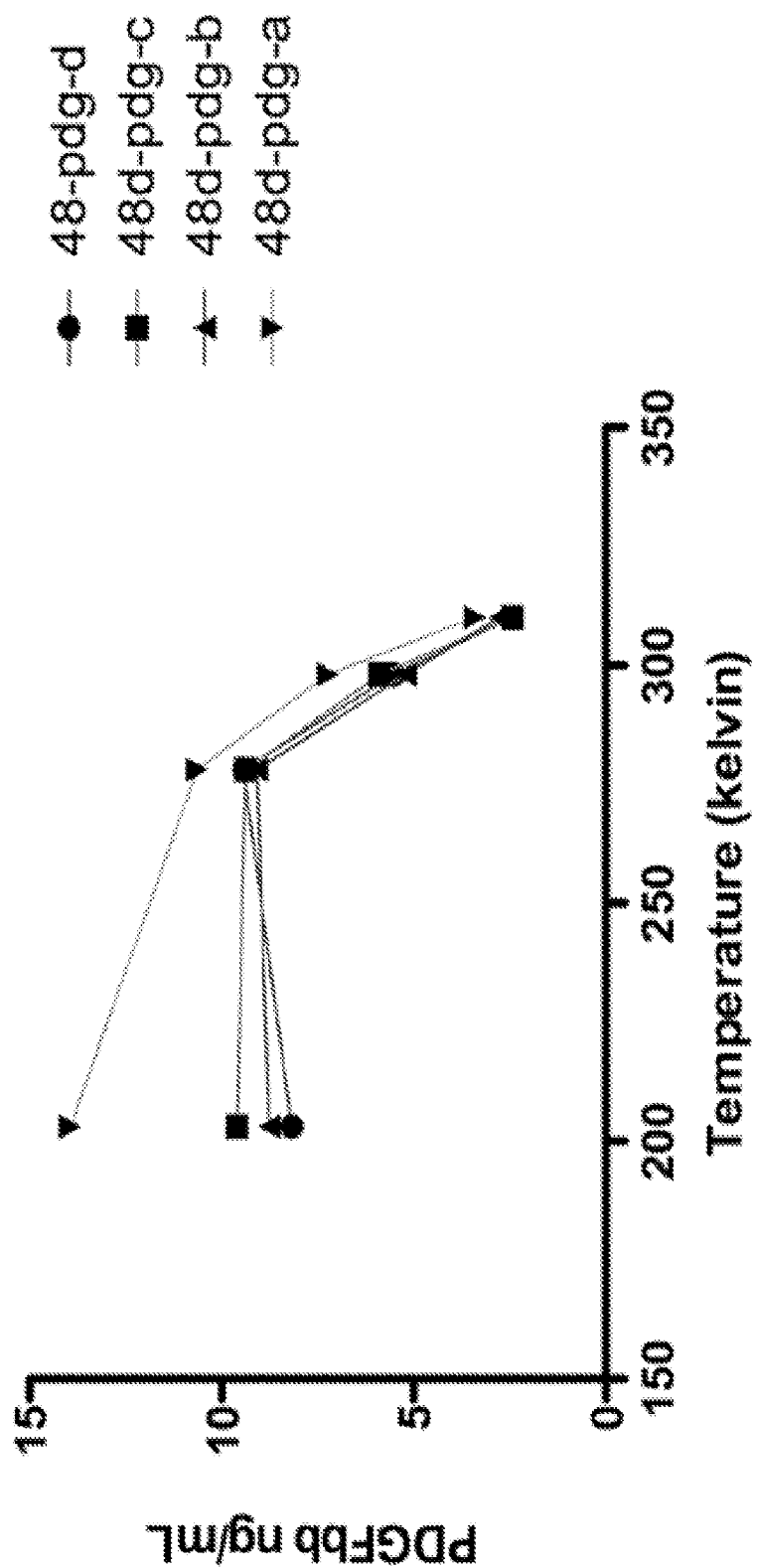
FIG. 33 is a graph plotting the amount of PDFG in PL samples incubated at the indicated temperatures.
Figure 34:
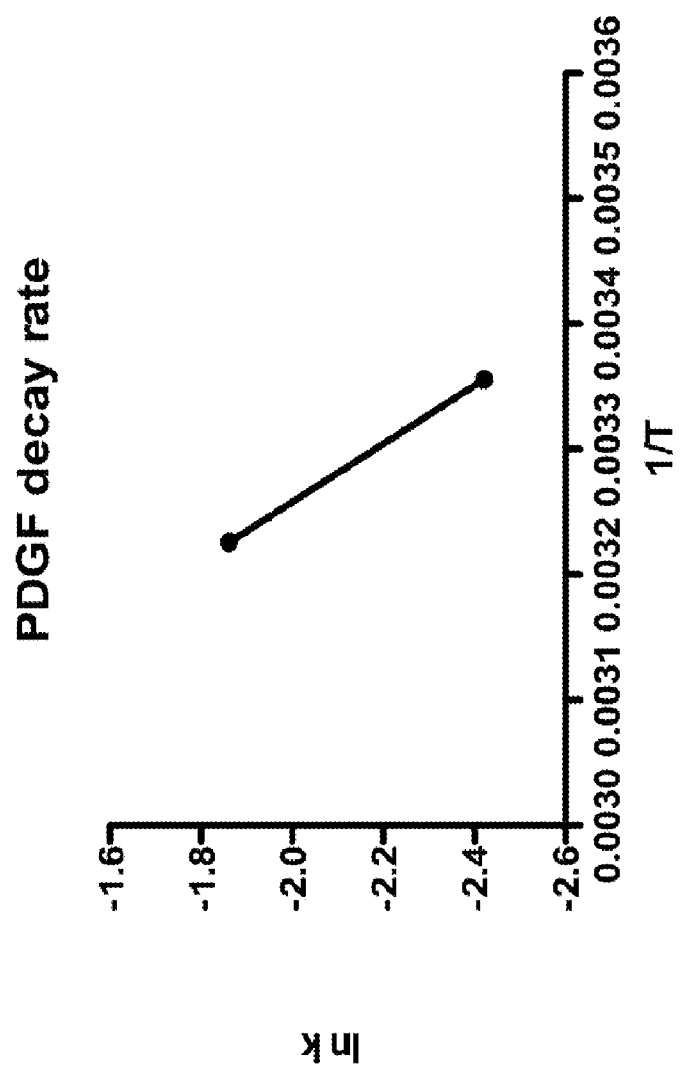
FIG. 34 is a graph plotting the PDFG decay rate.

PDGF was the most sensitive to the effects of accelerated aging. Therefore, the shelf life results were derived from that data (FIG. 33). The slope intercept method (Arrhenius equation), Q rule, and conservative approaches were used to estimate the shelf life of platelet lysates (FIG. 34 and Table 1).

TABLE 1

Estimated shelf life of platelet lysates.

|  | For storage at −70° C. | For storage at −20° C. |
|---|---|---|
| Shelf life | 24.1 years | Approximately 1 year (290.5 days) |

Taken together, these results indicate that the compositions provided herein containing platelet contents have an estimated shelf life of greater than five years at −70° C. and an estimated shelf life of about one year at −20° C.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A stable human platelet lysate composition comprising: a lysed platelet preparation comprising:
    i) plasma,
    ii) a total protein concentration of at least about 35 mg per mL,
    iii) a protein fraction that contains growth factor activity;
    iv) greater than 200 pg human VEGF per mL; and
    wherein said platelet lysate composition comprises protein complexes greater than 50 kDa.

2. The platelet lysate composition of claim 1, wherein the composition further comprises: about 180 pg/mL FGF.

3. The platelet lysate composition of claim 1, wherein the composition further comprises: about 54 ng/mL TGF-β.

4. The platelet lysate composition of claim 1, wherein the composition further comprises: about 8.5 ng/mL PDGF-BB.

5. The platelet lysate composition of claim 1, wherein the composition further comprises: about 180 pg/mL FGF; about 8.5 ng/mL PDGF; about 132 ng/mL IGF-1; and about 54 ng/mL TGF-β.

6. The platelet lysate composition of claim 1, wherein the total protein concentration is least about 48 mg per mL.

7. The platelet lysate composition of claim 1, wherein the platelet lysate composition is passed through a 0.20 µm or smaller filter after begin filtered by a 0.45 µm or smaller filter.

8. The platelet lysate composition of claim 1, wherein the composition further comprises heparin.

9. The platelet lysate composition of claim 1, wherein the composition is a spray, glue, or a suture.

10. The platelet lysate composition of claim 8, wherein the composition is a spray, glue, or a suture.

11. The platelet lysate composition of claim 1, wherein the protein fraction has a molecular weight of greater than 100,000 daltons.

* * * * *